United States Patent
DuPont et al.

(10) Patent No.: US 10,245,039 B2
(45) Date of Patent: Apr. 2, 2019

(54) METHODS AND APPARATUSES FOR APPLYING TENSILE FORCE TO TISSUE

(71) Applicant: Children's Medical Center Corporation, Boston, MA (US)

(72) Inventors: Pierre DuPont, Wellesley, MA (US); Dana Damian, Boston, MA (US); Veaceslav Arabagi, Cambridge, MA (US); Asghar Ataollahi, Brookline, MA (US); Assunta Fabozzo, Padua (IT)

(73) Assignee: Children's Medical Center Corporation, Boston, MA (US)

( * ) Notice: Subject to any disclaimer, the term of this patent is extended or adjusted under 35 U.S.C. 154(b) by 292 days.

(21) Appl. No.: 14/725,715

(22) Filed: May 29, 2015

(65) Prior Publication Data

US 2015/0342609 A1 Dec. 3, 2015

Related U.S. Application Data

(60) Provisional application No. 62/005,736, filed on May 30, 2014.

(51) Int. Cl.
*A61B 90/00* (2016.01)
*A61B 17/00* (2006.01)
*A61B 17/11* (2006.01)

(52) U.S. Cl.
CPC .......... *A61B 17/1114* (2013.01); *A61B 90/02* (2016.02); *A61B 2017/00022* (2013.01);
(Continued)

(58) Field of Classification Search
CPC . A61B 17/02; A61B 17/0206; A61B 17/1114; A61B 2017/00398;
(Continued)

(56) References Cited

U.S. PATENT DOCUMENTS

| | | | | |
|---|---|---|---|---|
| 5,649,960 A | * | 7/1997 | Pavletic | A61B 17/085 606/215 |
| 6,013,047 A | * | 1/2000 | King | A61M 25/0045 604/22 |

(Continued)

OTHER PUBLICATIONS https://www.bostonglobe.com/business/2013/10/27/bioroboticist-working-craft-device-correct-esophageal-birth-defect/Mn7uzdVaOM5AoYBJFyXqRO/story.html.*

(Continued)

*Primary Examiner* — Thaddeus B Cox

(74) *Attorney, Agent, or Firm* — Wolf, Greenfield & Sacks, P.C.

(57) ABSTRACT

Methods and apparatuses relate to an implantable apparatu0s that may be used to apply tensile force(s) to one or more tissue regions (e.g., proximal and distal esophagus portions, bowel, other conduits) within the body. Such tensile force(s) may cause stretch and/or growth of the tissue region(s). In various embodiments, support members (e.g., suture rings) may be attached to respective tissue regions. The support members may accommodate attachment of a number of sutures along the tissue region. Upon suitable attachment of the support member(s) to the tissue region(s), the actuator may be coupled to the support member(s). The actuator may then be controlled so as to cause relative movement between the support members toward or away from one another. Such movement may result in the application of appropriate tensile force(s) to the tissue region(s).

25 Claims, 16 Drawing Sheets

(52) U.S. Cl.
CPC ............... *A61B 2017/00398* (2013.01); *A61B 2017/1103* (2013.01); *A61B 2017/1132* (2013.01); *A61B 2090/064* (2016.02)

(58) Field of Classification Search
CPC .... A61B 2017/0212; A61B 2017/0287; A61B 90/02; A61F 2/0004; A61F 2/0031–2/0036; A61F 2/0045; A61F 2/0063
See application file for complete search history.

(56) References Cited

U.S. PATENT DOCUMENTS

| | | | | |
|---|---|---|---|---|
| 2005/0010191 | A1* | 1/2005 | Skinner | A61B 90/02 604/500 |
| 2006/0089571 | A1* | 4/2006 | Gertner | A61B 17/0401 600/593 |
| 2008/0027483 | A1* | 1/2008 | Cartledge | A61B 5/061 606/201 |
| 2009/0240339 | A1* | 9/2009 | Teitelbaum | A61F 2/04 623/23.64 |
| 2010/0191253 | A1* | 7/2010 | Oostman, Jr. | A61B 17/0206 606/133 |
| 2010/0261950 | A1* | 10/2010 | Lund | A61F 2/0045 600/30 |
| 2012/0150213 | A1* | 6/2012 | Gordon | A61B 17/0206 606/201 |

OTHER PUBLICATIONS

Alfaro et al., Are patients who have had a tracheoesophageal fistula repair during infancy at risk for esophageal adenocarcinoma during adulthood? J Pediatr Surg. Apr. 2005;40(4):719-20.
Appignani et al., Intestinal bypass of the oesophagus: 117 patients in 28 years. Pediatr Surg Int. 2000;16(5-6):326-8.
Azar et al., Esophageal replacement with transverse colon in infants and children. J Pediatr Surg. Feb. 1971;6(1):3-9.
Bax , Jejunum for bridging long-gap esophageal atresia. Semin Pediatr Surg. Feb. 2009;18(1):34-9.
Byrne et al., A new treatment for patients with short-bowel syndrome. Growth hormone, glutamine, and a modified diet. Ann Surg. Sep. 1995;222(3):243-54; discussion 254-5.
Cusick et al., Development of a technique for jejunal interposition in long-gap esophageal atresia. J Pediatr Surg. Aug. 1993;28(8):990-4.
Damian et al., Robotic implant to apply tissue traction forces in the treatment of esophageal atresia. Proceedings of the 2014 IEEE International Conference on Robotics and Automation (ICRA). pp. 786-792, May 31-Jun. 7, 2014 doi: 10.1109/ICRA.2014.6906944.
Dupont et al., Robotic tissue-growth implant to treat orphan diseases of the GI tract. 2014 Boston Investment Conference. Benefitting Research at Boston Children's Hospital. 1 page.
Erdoğan et al., Esophageal replacement using the colon: a 15-year review. Pediatr Surg Int. 2000;16(8):546-9.
Foker et al., A flexible approach to achieve a true primary repair for all infants with esophageal atresia. Semin Pediatr Surg. Feb. 2005;14(1):8-15.

Foker et al., Development of a true primary repair for the full spectrum of esophageal atresia. Ann Surg. Oct. 1997;226(4):533-41; discussion 541-3.
Foker et al., Long-gap esophageal atresia treated by growth induction: the biological potential and early follow-up results. Semin Pediatr Surg. Feb. 2009;18(1):23-9.
Freeman et al., Colon interposition: a modification of the Waterston technique using the normal esophageal route. J Pediatr Surg. Feb. 1982;17(1):17-21.
Hendren et al., Electromagnetic bougienage to lengthen esophageal segments in congenital esophageal atresia. N Engl J Med. Aug. 28, 1975;293(9):428-32.
Hendren et al., Esophageal atresia treated by electromagnetic bougienage and subsequent repair. J Pediatr Surg. Oct. 1976;11(5):713-22.
Hirschl et al., Gastric transposition for esophageal replacement in children: experience with 41 consecutive cases with special emphasis on esophageal atresia. Ann Surg. Oct. 2002;236(4):531-9; discussion 539-41.
Lavasani et al., Muscle-derived stem/progenitor cell dysfunction limits healthspan and lifespan in a murine progeria model. Nat Commun. Jan. 3, 2012;3:608. doi: 10.1038/ncomms1611.
Martinez et al., Elastomeric Origami: Programmable Paper-Elastomer Composites as Pneumatic Actuators. 2012 Adv. Funct. Mater., 22: 1376-1384. doi:10.1002/adfm.201102978.
McCluskey, Mom fights to give child a normal life. Boston Herald. Apr. 30, 2014. http://www.bostonherald.com/news_opinion/local_coverage/2014/04/mom_fights_to_give_child_a_normal_life [last accessed Nov. 19, 2015]. 3 pages.
Oehlerking et al., A hydraulically controlled nonoperative magnetic treatment for long gap esophageal atresia. 2011 J. Med. Devices; 5(2):027511.
Olieman et al., Interdisciplinary management of infantile short bowel syndrome: resource consumption, growth, and nutrition. J Pediatr Surg. Mar. 2010;45(3):490-8. doi: 10.1016/j.jpedsurg.2009.08.009.
Pinheiro et al., Current knowledge on esophageal atresia. World J Gastroenterol. Jul. 28, 2012;18(28):3662-72. doi: 10.3748/wjg.v18.i28.3662.
Pultrum et al., Development of an adenocarcinoma of the esophagus 22 years after primary repair of a congenital atresia. J Pediatr Surg. Dec. 2005;40(12):e1-4.
Rintala et al., Outcome of esophageal atresia beyond childhood. Semin Pediatr Surg. Feb. 2009;18(1):50-6. doi: 10.1053/j.sempedsurg.2008.10.010.
Schiller et al., Evaluation of colonic replacement of the esophagus in children. J Pediatr Surg. Dec. 1971;6(6):753-60.
Sherman et al., Oesophageal reconstruction in children using intrathoracic colon. Arch Dis Child. Feb. 1957;32(161):11-6.
Spencer et al., Enterogenesis in a clinically feasible model of mechanical small-bowel lengthening. Surgery. Aug. 2006;140(2):212-20.
Stone et al., Esophageal replacement with colon interposition in children. Ann Surg. Apr. 1986;203(4):346-51.
Woolley et al., Esophageal atresia types A and B: upper pouch elongation and delayed anatomic reconstruction. J Pediatr Surg, Feb. 1969;4(1):148-53.
Zaritzky et al., Magnetic compression anastomosis as a nonsurgical treatment for esophageal atresia. Pediatr Radiol. Sep. 2009;39(9):945-9. doi: 10.1007/s00247-009-1305-7. Epub Jun. 9, 2009.

* cited by examiner

METHODS AND APPARATUSES FOR APPLYING TENSILE FORCE TO TISSUE

CROSS-REFERENCE TO RELATED APPLICATIONS

This application claims the benefit under 35 U.S.C. § 119(e) to U.S. Provisional Application Ser. No. 62/005,736, entitled "METHODS AND APPARATUSES FOR APPLYING TENSILE FORCE TO TISSUE," filed on May 30, 2014, the entirety of which is herein incorporated by reference.

BACKGROUND

1. Field

Aspects herein relate to the application of tensile force to a tissue region, such as a portion of the gastrointestinal system.

2. Discussion of Related Art

Esophageal atresia is a medical condition where a section of the esophagus is missing. Esophageal atresia may be congenital where, for example, a proximal esophagus portion ends in a pouch rather than connecting normally to the stomach. Or, esophageal atresia may arise due to a surgical need to remove a segment of the esophagus. As shown in FIG. 1, the esophagus 10 is split into a proximal esophagus portion 12 and a distal esophagus portion 14, failing to provide a continuous passageway from the mouth 16 to the stomach 18.

Treatment for esophageal atresia may involve connecting the two end segments of the esophagus to each other. This is usually done through a series of incisions between the ribs on the right side of the child and mechanically manipulating the proximal and distal segments of the esophagus so as to ultimately be joined through surgical anastomosis. In some cases, called long-gap esophageal atresia, the gap between proximal and distal esophageal segments may be excessive (e.g., greater than 3 cm long) and cannot be corrected during a single surgery. For long-gap esophageal atresia, various surgical approaches have been used, such as removal and insertion of another digestive segment of the patient, such as the colon or jejunum.

An advanced surgical treatment called the Foker method has been used to elongate and then join together the esophageal segments, typically when the patient is at 3 months of age or older. When using the Foker method, surgeons stitch traction sutures 50 into the esophageal ends 12, 14 at respective locations 52, 54. The sutures 50 are wrapped around the ribs 20, which are used as pulleys, and tied off outside of the back of the patient. The suture loops are tightened daily so as to cause stretching or growth of the respective esophageal segments until the ends are close enough to be joined together. A shortcoming of the Foker method is that the patient needs to be kept paralyzed and sedated for the entire duration of treatment where traction forces are applied, which is commonly 1-4 weeks. Otherwise, absent paralysis and sedation, certain types of motion of the rib cage may result in undesirable tearing of the sutures out of the respective esophageal segments to which they are attached. Though, paralysis and sedation for such long periods of time may lead to increased risk in patient morbidity (e.g., pneumonia, bone loss, etc.).

SUMMARY

The inventors have appreciated that it is desirable to minimize the amount of time in which patients are paralyzed and sedated, while also minimizing risks of esophageal tearing. The inventors have appreciated that it would be advantageous to apply tensile force(s) (e.g., traction force) to one or more tissue regions within the body so as to induce stretch and/or growth thereof, in a manner that is safe, comfortable and effective.

Accordingly, an actuator, or other suitable device that controls or otherwise causes mechanical movement, may be implanted within the body at the site where the tensile force is to be applied. Support members (e.g., suture rings) may be attached to respective tissue regions, such as proximal and distal esophageal portions, or other tissue conduits within the body. The support members may each include an arcuate portion that accommodates attachment of a number of sutures along a boundary (e.g., circumference) of the tissue region.

Once the support members are firmly secured to the tissue regions, the actuator may be coupled thereto. The actuator may then be controlled so as to cause relative movement between the support members toward or away from one another, which results in the application of appropriate tensile force(s) to the tissue region(s).

In an illustrative embodiment, an implantable apparatus for applying force to bodily tissue is provided. The apparatus includes an actuator having a first anchor portion and a second anchor portion, the actuator configured to cause relative movement of the first anchor portion and the second anchor portion toward or away from one another; a first support member constructed to be attached to a first tissue region and adapted to be coupled to the first anchor portion of the actuator; and a second support member constructed to be attached to a second tissue region and adapted to be coupled to the second anchor portion of the actuator, wherein relative movement of the first anchor portion and the second anchor portion toward or away from one another results in application of a tensile force to at least one of the first tissue region and the second tissue region.

In another illustrative embodiment, an implantable support member for use in applying force to bodily tissue is provided. The support member includes an arcuate portion adapted to accommodate attachment of a plurality of sutures along a circumference of a tissue region; and a coupling portion constructed and arranged to couple the arcuate structure with an anchor portion of an actuator for movement of the arcuate portion along an axial direction of the tissue region.

In yet another illustrative embodiment, a method of using an implantable actuator to apply force to bodily tissue is provided. The method includes attaching a first support member to a first tissue region; attaching a second support member to a second tissue region; positioning the implantable actuator within a body cavity adjacent to the first tissue region and the second tissue region; and controlling the actuator to cause relative movement of the first support member and the second support member toward or away from one another resulting in application of a tensile force to at least one of the first tissue region and the second tissue region.

In another illustrative embodiment, an implantable apparatus for applying force to a bodily conduit is provided. The apparatus may include an actuator constructed and arranged to couple with a first tissue region of the bodily conduit and a second tissue region of the bodily conduit and cause relative movement of the first tissue region and the second tissue region toward or away from one another resulting in application of a tensile force to at least one of the first tissue region and the second tissue region.

In another illustrative embodiment, a method of using an implantable actuator to apply force to a bodily conduit is provided. The method may include coupling a first portion of the actuator to a first tissue region; coupling a second portion of the actuator to a second tissue region; positioning the implantable actuator within a body cavity adjacent to the first tissue region and the second tissue region; and controlling the actuator to cause relative movement of the first tissue region and the second tissue region toward or away from one another resulting in application of a tensile force to at least one of the first tissue region and the second tissue region.

Various embodiments of the present invention provide certain advantages. Not all embodiments of the invention share the same advantages and those that do may not share them under all circumstances. Various embodiments described may be used in combination and may provide additive benefits.

Further features and advantages of the present invention, as well as the structure of various embodiments of the present invention are described in detail below with reference to the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various embodiments of the invention will now be described, by way of example, with reference to the accompanying drawings, in which.

DETAILED DESCRIPTION

Figure 1:
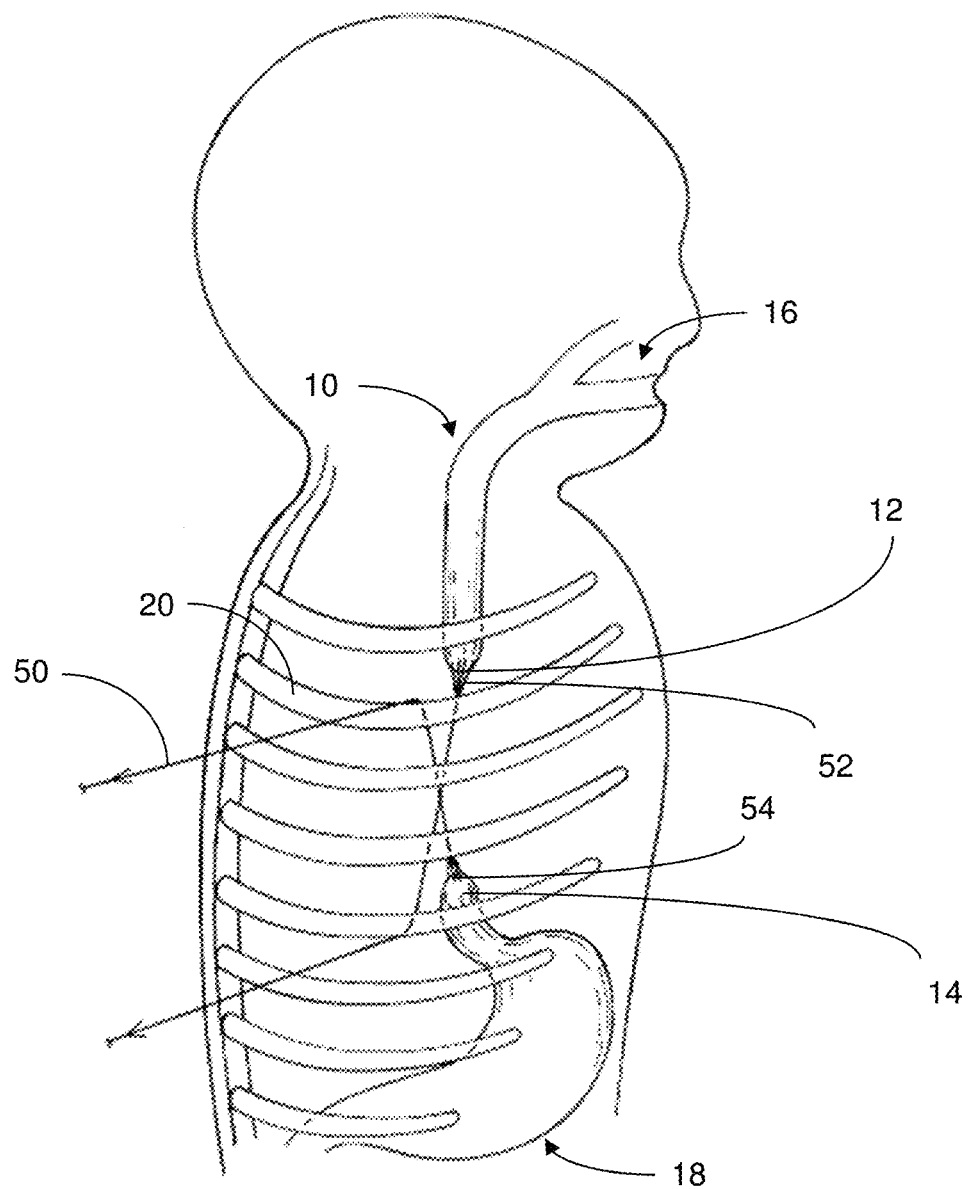
FIG. 1 shows a schematic of a medical condition being treated using a conventional method.

The present disclosure relates to the ability to cause elongation and/or growth of one or more tissue regions, such as conduits from the gastrointestinal system, (e.g., esophagus, intestine, bowel, or other tube), by grasping the region and applying an appropriate tensile force thereto. The inventors have recognized that it would be beneficial to provide a method and apparatus to apply tensile force to one or more tissue regions without having to paralyze and sedate the patient for long periods of time, which is often required by existing techniques such as the Foker method for treating esophageal atresia. To do this, rather than extending sutures from the tissue region(s) of interest around bodily structures, such as portions of the rib cage, an actuator may be implanted directly at the site of the tissue region(s). Accordingly, the implanted actuator may be configured so as to apply the tensile force(s) to the tissue region(s) directly, without generating undesirable reactive forces or torques on surrounding areas of the body (e.g., ribs), which may lead to unnecessary load bearing or injury.

As noted herein, the application of tensile force to a tissue region of the body may include traction force treatment, which involves pulling on a part of the body so as to impart tension to the body part.

As an example, discussed in further detail below, to treat esophageal atresia, a first surgery is performed to attach (e.g., sew) a first suture ring to the proximal esophagus portion and also to attach a second suture ring to the distal esophagus portion. The suture rings may, in turn, be coupled to an actuator that is implanted adjacent to (e.g., alongside, in alignment with) the proximal and distal esophagus portions.

Then, without having to keep the patient paralyzed and sedated, the actuator may then cause relative movement of the suture rings toward one another so as to apply a suitable tensile force to the proximal and distal esophagus portions. That is, once the actuator is implanted, the patient may regain consciousness so as to remain suitably active during tensile force treatment. This tensile force may cause stretching and/or growth of the esophagus tissue so as induce elongation of the disconnected tissue segments toward one another.

Because the actuator is implanted at the site where the tensile forces are applied, undesirable reaction forces and torques that may otherwise arise when suture threads are wrapped around surrounding areas of the body (e.g., ribs, back, surrounding tissue) are avoided. In other words, the actuator may generate forces that effectively cancel each other, resulting in an overall minimal net force applied to the body.

In addition, because the patient may be active during treatment, such tensile force(s) may be applied in a relatively gradual manner, over a longer period of time than would otherwise be the case if the patient were under anesthesia.

When opposing portions of the esophagus are sufficiently elongated (e.g., suitably overlapping due to laterally offset support members, or pressed against one another via axially aligned support members), a second surgery is performed to join the tissue segments, and remove the implanted actuator and suture rings.

It can be appreciated that aspects of the present disclosure are not limited to treatment of the esophagus. For example, methods and apparatuses described herein may be employed to apply tensile forces to other tissue regions, such as the bowel, other portions of the intestines, blood vessels, or other appropriate portions of the body. For example, in short bowel syndrome, the small intestine is too short (e.g., due to a congenital malformation or removal of a portion of the small intestine) to enable sufficient absorption of nutrients from food passing therethrough. In accordance with the present disclosure, suitable tensile forces may be applied to the bowel, or other intestinal area, so as to stretch, grow or otherwise replace the missing tissue and, hence, restore normal quality of life.

Figure 2:
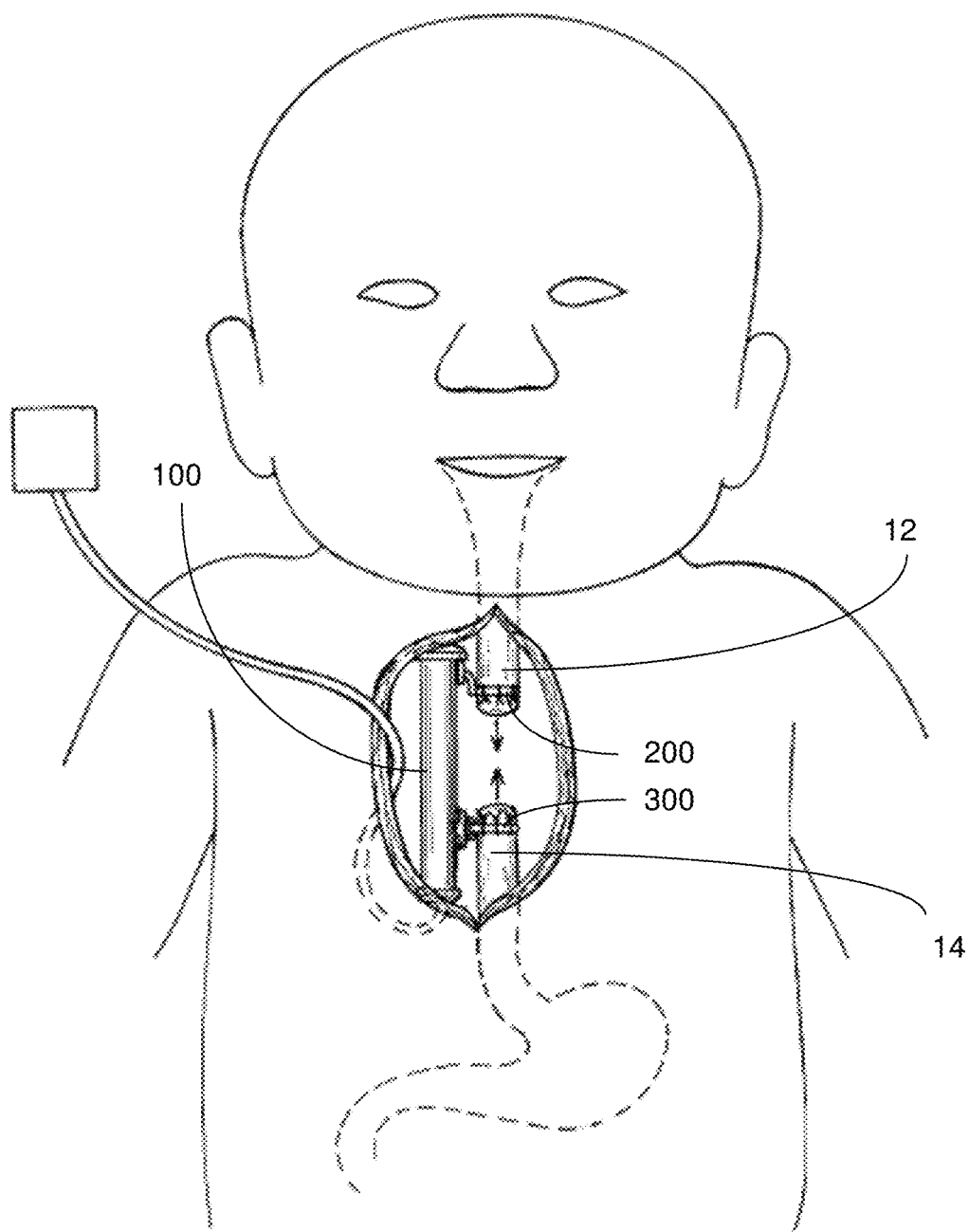
FIG. 2 illustrates an implantable apparatus and method of treatment of the medical condition in accordance with an embodiment.

FIG. 2 depicts an illustrative embodiment of an implantable apparatus having an actuator 100 and support members 200, 300 coupled to respective anchor portions of the actuator 100. The proximal support member 200 is attached to the proximal esophagus portion 12 and the distal support member 300 is attached to the distal esophagus portion 14. The actuator 100 is configured to move the respective anchor portions and, hence, the support members 200, 300 toward or away from one another so as to apply an appropriate amount of tensile forces to the respective proximal and distal esophagus portions 12, 14.

It can be appreciated that the actuator 100 may have any suitable configuration that allows for the support members 200, 300 to be appropriately controlled. For example, as discussed herein, the anchor portion(s) of the actuator may provide suitable structure to which the respective support member(s) may be coupled, so that the support member(s) may be mechanically controlled or moved. While various embodiments of actuators are described herein, the present disclosure is not limited to any particular arrangement.

As shown, the actuator 100 is positioned on the right side of the chest, away from the heart, adjacent the right lung. In some embodiments, implantation of the actuator 100 causes slight displacement of the right lung from its normal position. Though, in some cases, the actuator 100 is small enough such that minimal displacement or compression of surrounding tissue (e.g., lung, main stem bronchus) occurs, if at all.

The weight of the actuator 100 may be at least partially supported by the opposing esophageal segments 12, 14. In some embodiments, the actuator 100 may also be supported by surrounding tissue. For example, as discussed further below, the actuator 100 may be covered by an elastomeric material which, in turn, may be attached and, hence, supported by relatively sturdy surrounding tissue. Accordingly, the actuator 100 may be suitably suspended while disposed adjacent to the esophageal segments without causing undesirable strain to the surrounding tissue(s).

Figure 3:
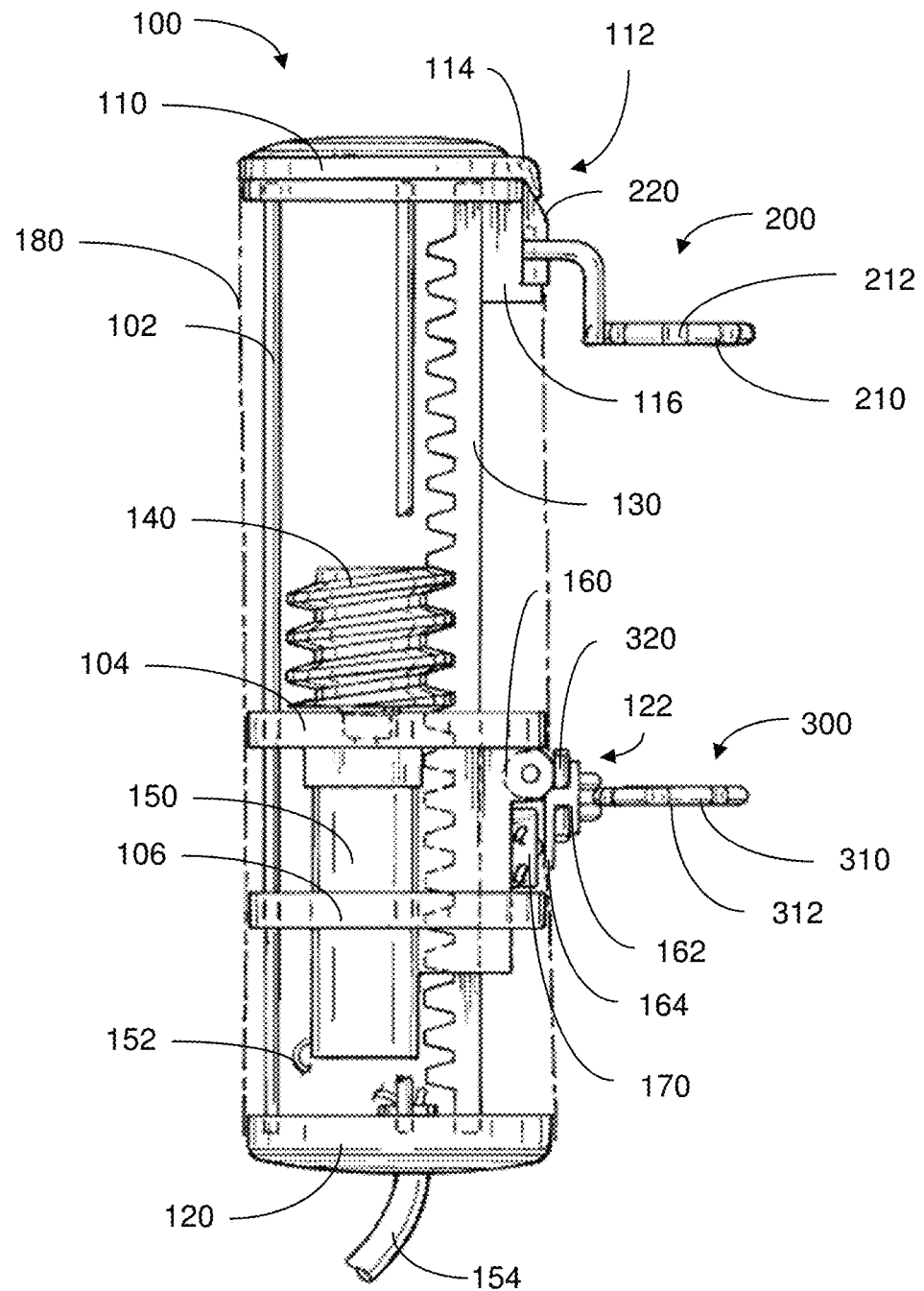
FIG. 3 depicts a plan view of an implantable apparatus in accordance with an embodiment.

FIG. 3 illustrates an embodiment of an actuator 100 having a proximal end 110 and a distal end 120 for enclosing various components of the actuator. The actuator 100 further includes support rods 102 that extend between the proximal and distal ends, providing structural stability to the assembly. The support rods 102 may provide overall structural support for the actuator 100; though, in some embodiments, the support rods 102 are formed of a low-friction surface or are lubricated so as to promote sliding of various components (e.g., covering, carrier) there along. As described more below, a covering 180 may extend between the proximal and distal ends for further enclosing components of the actuator, and for providing additional protection and support thereof.

As shown in this embodiment, the actuator 100 may have a rack and pinion type arrangement, including a track 130, an actuating element 140 and a motor 150. The motor 150 (e.g., DC motor, AC motor, etc.) is coupled to the actuating element 140 which, in turn, is configured to move back and forth along the track 130 upon activation of a motor 150. Here, the track 130 is depicted as a rack and the actuating element 140 is shown as a worm gear having threads that complement the teeth of the rack. Accordingly, upon activation of the motor 150, the actuating element 140 (worm gear) is rotated so as to result in movement thereof back and forth along the track 130 (rack), depending on its direction of rotation.

It should be appreciated that the actuator 100 may have any suitable configuration for controlling, imparting or otherwise causing mechanical motion. For example, rather than a rack and pinion type arrangement, the actuator may include a precision screw drive. Or, multiple actuating elements and/or motors may be employed, for example, to provide independent movement control of the anchor portions and/or support members coupled thereto. Alternatively, as discussed further below, the actuator may incorporate a spool or pulley-type arrangement where tensioning elements (e.g., suture threads) are used to pull opposing anchor portions and/or support members together. In some embodiments, the actuator may include a spring-like material (e.g., passive spring) arranged to bias the support members and/or anchoring portions toward or away from one another as desired, without any need for sensors or electronics. The actuator may employ a shape changing material (e.g., shape memory alloy/polymer) that changes shape over time so as to drive actuation. Various non-electric mechanisms that produce force variations with time may also be employed, such as escapement mechanisms found in mechanical watches, as commonly known to those of skill in the art.

It can also be appreciated that an actuator does not require a motor to drive mechanical motion. For example, an actuator may be driven pneumatically, hydraulically, electrochemically, mechanically, etc., without requiring the application of outside electrical power. Accordingly, embodiments of the present disclosure need not be limited to a motor, as an actuator is understood herein as a device that causes or controls mechanical movement.

As further shown in FIG. 3, the actuating element 140 is coupled to a carrier 160, which moves with the actuating element 140 back and forth along the track 130. The carrier 160 and the actuating element 140 are held in place with respect to one another via mounting members 104, 106, provided as support rings. The mounting members are also arranged so as to move with the actuating element 140 and carrier 160 along the track 130, providing support thereto. For instance, the mounting members 104, 106 may have holes through which the support rods 102 extend. Thus, the mounting members may move along the support rods. By providing support for the carrier 160, the mounting members 104, 106 may also be arranged so as to reduce stresses on the covering 180 that may otherwise arise to due motion of the carrier.

The carrier 160 may be an extension of a distal anchor portion 122, which includes an attachment structure that allows for attachment of a distal support member 300 thereto. For example, the attachment structure may include an outer plate 162 and an inner plate 164 that serve to hold or otherwise coupled with the distal support member 300, as discussed further below.

In this non-limiting example, a force sensor 170 is further coupled to the carrier 160, for sensing the force(s) applied to the distal support member 300 and, hence, the tissue region to which it is attached. In some embodiments, the force sensor may be mounted in such a manner so as to resist rotational movement or other displacement of the distal support member 300 against the sensor. Thus, the force(s) acting on the distal support member 300 (and, hence, the tissue region to which the support member is attached) may be monitored upon movement of the distal support member 300, caused by activation of the actuator 100.

While not expressly shown in the figures, other sensors configured to sense relevant information, for example, related to the tensile force(s) applied to the tissue region(s), or displacement of the support member(s) and/or tissue region(s), may be employed. For example, a linear potentiometer may be employed to determine the relative distance between support members at any given moment. Such a potentiometer may be mounted to an associated rack, or alternatively may be arranged so as to measure motor revolutions from the motion of a support member (e.g., support ring), which may provide an indication as to the distance between support members. Or, in some embodiments, a sensor for acquiring information regarding tissue perfusion may be employed, and tensile force applied to the tissue region(s) may be controlled based on this information.

Figure 4A:
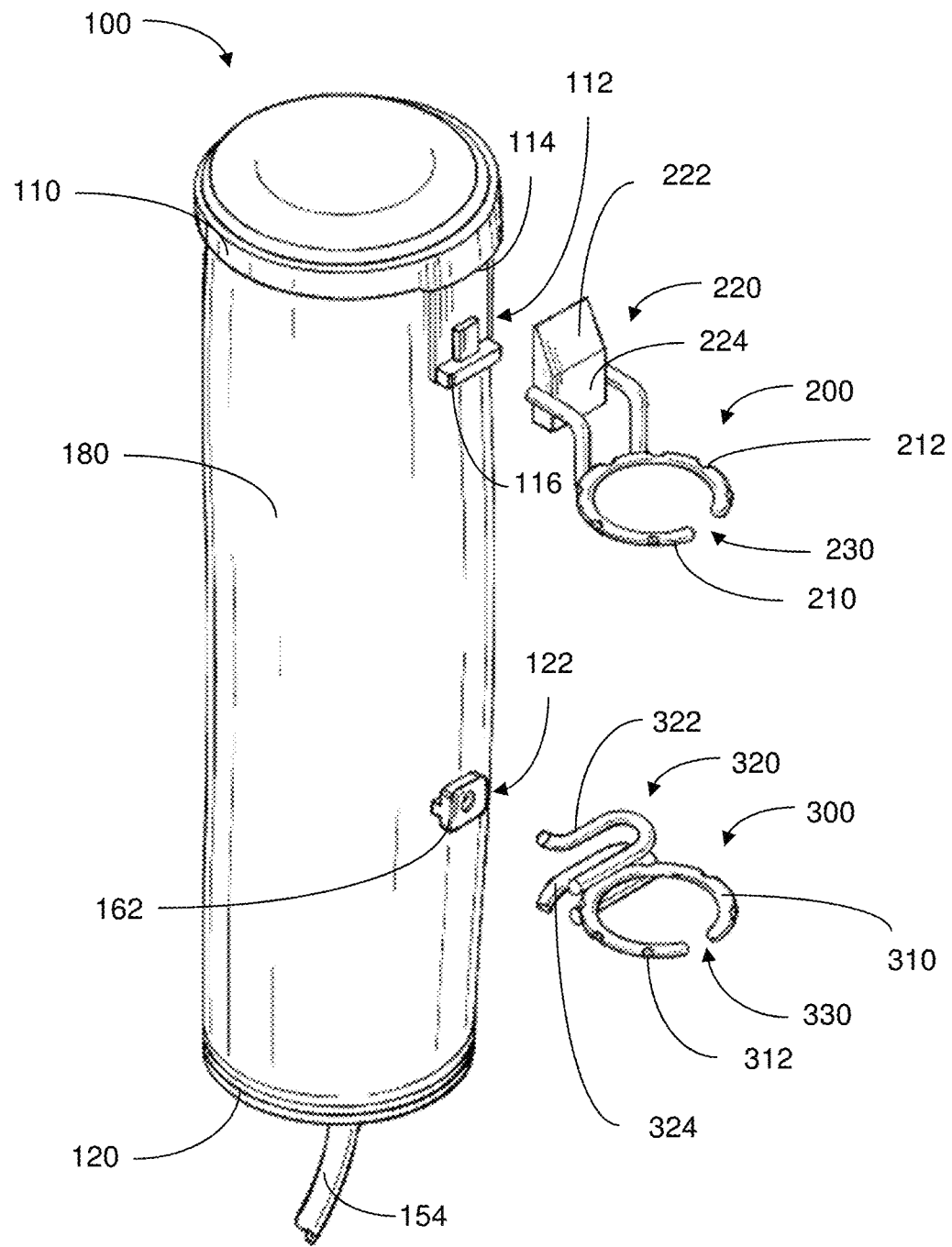
FIG. 4a illustrates a perspective view of various components of an implantable apparatus in accordance with an embodiment.

FIG. 4a shows an illustrative embodiment of the actuator 100, the proximal support member 200 and the distal support member 300, each support member defining an area within which a tissue region may be suitably positioned. Here, the support members 200, 300 are depicted as suture rings that are sized and shaped for attachment to opposing esophageal segments. That is, the proximal support member 200 is configured to be attached to the proximal esophagus portion 12, and the distal support member 300 is configured to be attached to the distal esophagus portion 300.

It can be appreciated that the support members may have any suitable configuration. For example, the support members may be configured (e.g., sized and shaped) for attachment to another tissue region within the body, such as the bowel, other parts of the intestines or gastrointestinal tract, blood vessels, tissue regions other than conduits, etc.

As shown in this embodiment, each of the support members 200, 300 include an arcuate portion 210, 310 that is substantially ring-shaped. Accordingly, the arcuate portion of the support members may accommodate attachment of a number of sutures along the circumference of a tissue conduit to which tensile force is to be applied.

Each of the arcuate portions 210, 310 may optionally have a number of recessed regions 212, 312 that are substantially evenly distributed or spaced along the arcuate surface. The recessed regions 212, 312 allow for sutures to be substantially retained within the space defined therein. As shown, the recessed regions 212, 312 may be notches or grooves located on an outer edge of the arcuate portion 210, 310. In some embodiments, the notches or grooves may be located on an inner edge of the arcuate portions. Or, the recessed regions may include holes that extend through the arcuate portions of the support members. By retaining the sutures within the recessed regions, the sutures are prevented or otherwise hindered from slipping or sliding in an undesirable manner around the circumference of the ring, and maintain their position(s) along the support member.

In some embodiments, and as shown in FIG. 4a, the support members 200, 300 may have arcuate portions 210, 310 that are constructed such that a gap 230, 330 exists between respective ends of the arcuate surface. The open ring structure, including the gap 230, 330, of the support members allows for a tissue conduit to easily slip inside the area defined by the ring. For example, rather than having to fit the ring over the end of the tissue conduit (e.g., pouch of the proximal or distal esophagus portion) and then slide the ring to a preferred location, the tissue conduit may be suitably folded so as to be inserted through the gap 230, 330 and directly into the area surrounded by the ring. Though, in some embodiments, rather than an open configuration, the ring could have a closed configuration, without a gap in the arcuate portion.

In some embodiments, aspects of the support members 200, 300, or the entire support members (e.g., rings) themselves may be structurally identical with one another. This allows for the support members to be mutually interchangeable. That is, a distal support member may be used as a replacement for a corresponding proximal support member, and vice versa. For example, the proximal support member may include prongs and the proximal anchor portion may include a recessed arrangement within which the prong may slide or otherwise fit, similar to that described above with respect to the distal support member.

When treating short bowel syndrome, the tissue conduit to be treated is connected, rather than segmented, without an end for the ring to fit over. Accordingly, in such cases, it may be preferable for the support member to have an open ring structure. As a result, the conduit may slide through the gap of the ring so that the ring circumscribes the conduit.

In some embodiments, as presented above, the ring may be situated on the outside of the tissue conduit, for example, for ease of implantation. Though, in other embodiments, the ring(s), or support member having another shape, may be implanted on the inside of the tissue conduit(s). In an embodiment, a ring may include a hinge to allow a closed ring to open and thereby allow the ring to surround the tissue conduit. Other embodiments of support members are possible.

In various embodiments, multiple support members may be utilized in combination. That is, support members may include suture rings, sutures, or other suitable components that may allow for appropriate tensile forces to be applied to the tissue region(s). For example, as noted above, a suture ring may be positioned around a tissue conduit and sutures may serve to attach the suture ring thereto. Alternatively, for some embodiments, a suture ring is not required. For instance, the support member may include sutures, or other flexible materials, that are attached to the tissue region(s) of interest and the sutures may be coupled to anchor portions of an actuator for pulling the tissue region(s) in a suitable manner.

In various embodiments, the support members 200, 300 may also include respective coupling portions 220, 320 that allow for attachment and detachment of the support members to corresponding parts of the actuator 100. Accordingly, the support members 200, 300 may be sutured or otherwise attached to the appropriate tissue regions and then coupled to the actuator.

As shown in FIG. 4a, the proximal support member 200 has a coupling portion 220 that has structure complementary to that of the proximal anchor portion 112 of the actuator in a manner so as to be reversibly attachable to one another. As further shown, upon attachment, the proximal support member 200 remains exterior to the covering 180 of the actuator 100. Accordingly, the covering 180 may include an opening that allows for the proximal support member 200 and the proximal anchor portion 112 to be coupled to one another such that the proximal support member 200 extends or remains outside of the covering 180. The anchor portion(s) may be configured so that coupling of the respective support member(s) thereto can be made without compromising the protection provided by the covering 180. For example, anchor portions may be arranged such that penetration of a sealed region formed by the covering may be avoided.

The covering 180 may further accommodate relative movement of the anchor portion(s) toward or away from one another. For example, the material of the covering may be sufficiently flexible to allow for displacement of the anchor portion(s) up and down the body of the actuator. Or, the covering may include slits or openings (not shown in the figures) that permit repositioning of the anchor portion(s) along the body of the actuator.

In this embodiment, the proximal anchor portion 112 optionally includes an overhanging cap 114 under which an upper plate 222 of the coupling portion 220 of the support member 200 may slide and a shelf 116 on which a lower plate 224 of the coupling portion 220 may rest. In an example, when coupling the support member 200 to the proximal anchor portion 112, the lower plate 224 may be placed on to the shelf 116 and the overhanging cap 114 may be fitted over the top of the actuator and upper plate 222 so as to keep the proximal support member 200 firmly anchored in place during tensile force treatment. In this embodiment, the proximal anchor portion 112 remains in place along with other fixed components of the actuator, though, for instances where the proximal anchor portion 112 is configured to move, the proximal support member 200 may move therewith. In some cases, when coupling the support member 200 and the proximal anchor portion 112 together, there is little to no rubbing against the covering 180, thus, mitigating against or otherwise reducing abrasion.

As further shown, the distal support member 300 has a coupling portion 320 that has a structure complementary to that of the distal anchor portion 122, so as to be reversibly attachable to one another. In this embodiment, the distal anchor portion 122 includes a plate 162 that extends from the carrier 160. While, in this case, the carrier 160 remains inside of the covering 180, as shown in FIG. 4a, the plate 162 extends from a stem so as to be located outside of the covering 180. Accordingly, the plate 162 is positioned so as to be able to couple with the support member 300. The covering 180 may include an opening that allows for the distal support member 300 and the distal anchor portion 122 to be coupled to one another such that the distal support member 300 extends or remains outside of the covering 180.

As further shown in this embodiment, the plate 162 is positioned so as to provide space for prongs 322, 324 of the coupling portion 320 to slide or be inserted, for physical coupling therewith. For example, when coupling the distal support member 300 to the distal anchor portion 122, the upper prong 322 and the lower prong 324 may be fitted underneath the plate 162 and around the stem. In addition, when coupling the support member 300 and the distal anchor portion 122 together, little to no rubbing against the covering 180 occurs, thus, mitigating against or otherwise reducing abrasion. As a result, the distal support member 300 may be suitably anchored in place during tensile force treatment. Accordingly, upon activation of the actuator 100, the distal support member 200 moves along with the distal anchor portion 122. As provided for some embodiments, the support members are attached to the appropriate tissue regions and the actuator is subsequently coupled to the support members. The support member(s) may be attached to the actuator in any suitable manner.

Though, it can be appreciated that, for other embodiments, upon implantation, the support members may already be attached or coupled to the actuator. In such cases, when the support members are attached to appropriate tissue regions, an additional step in the installation procedure of coupling the actuator to the support members need not be taken.

Figure 4B:
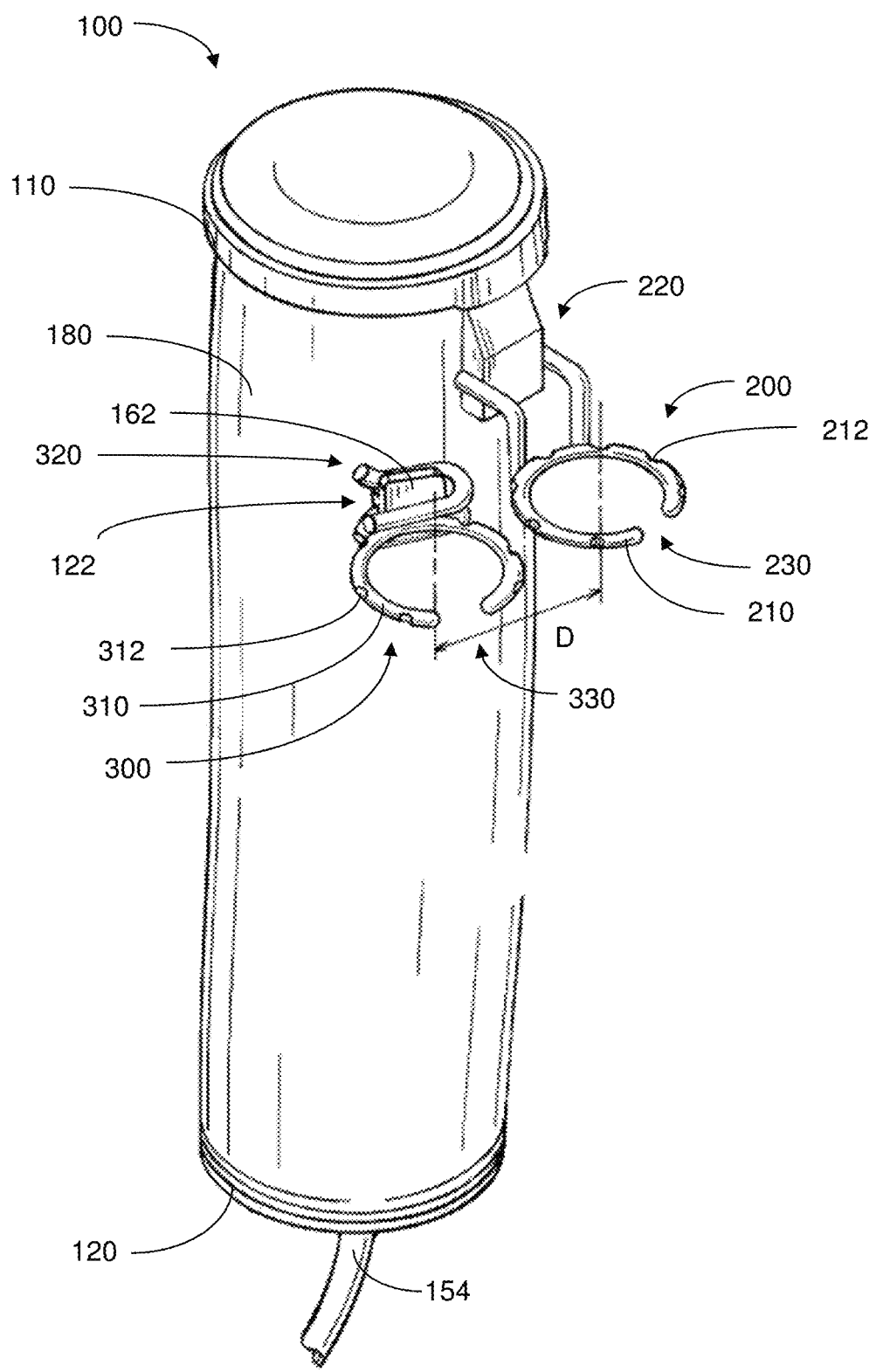
FIG. 4b shows a perspective view of an implantable apparatus in accordance with an embodiment.

In some embodiments, as shown in FIG. 4b, the support members may be arranged so as to be laterally offset a suitable distance D with respect to one another. Accordingly, when the offset distance D is sufficient, during tensile force application, the support members may be able to move past one another. This allows for opposing tissue regions to be stretched toward one another to a point where an appropriate amount of overlap therebetween arises, for subsequent joining thereof.

Though, when support members are laterally offset, during actuation, such a configuration may lead to the generation of a net torque. To prevent the overall apparatus from spinning or twisting, this net torque may be resisted, for example, by providing an appropriate support connection between the apparatus and the surrounding tissue. For instance, a support covering or other hammock-like arrangement may form an attachment between the apparatus and the surrounding tissue, keeping the implanted apparatus in place in the midst of actuation.

In some embodiments, proximal and distal support members, or parts of the actuator (e.g., anchor portions), may be appropriately imaged, so as to track their position upon implantation. For example, the support members, or parts of the actuator, may incorporate a radioactively traceable material, or may be visible through X-ray imaging.

As discussed above, the covering 180, along with support rods 102 and mounting members 104, 106, may provide a suitable degree of protection (e.g., ability to shield impact, waterproofing, providing a watertight seal, preventing tissue from bulging into the actuating mechanism(s)/component (s), etc.) for the various mechanical and electrical components of the actuator 100 from surrounding tissue. For example, the covering may provide protection for the internal electronics of the actuator as well as shield the body from possible contaminants and/or abrasion from the actuator. In some embodiments, the overall actuator structure exhibits a sufficient degree of rigidity to protect components of the actuator from the surrounding tissue, yet is sufficiently compliant so as to avoid the occurrence of damage or injury to the tissue itself. Accordingly, the support rods 102 and mounting members 104, 106 may provide the actuator 100 with a suitable level of sturdiness, and the covering 180 may act as a jacket that provides a barrier from direct contact between the internal components of the actuator and the surrounding tissue. In some embodiments, the covering 180 is clamped to the proximal and distal ends 110, 120 and the mounting members 104, 106, or other components of the actuator. The components of the actuator may also be structured such that portions of the covering do not encroach upon and/or jam the internal mechanism(s) of the actuator.

In some embodiments, an attachment may be formed between the covering and surrounding tissue (e.g., chest wall), so as to provide support for the weight of the actuator and/or support members. Or, for some embodiments, an additional covering or an extension of the covering of the actuator (not shown in the figures) may be wrapped or otherwise placed around the implanted apparatus and the tissue region(s) to be treated. This additional covering or covering extension may be attached to relatively strong surrounding tissue so as to provide support for the apparatus during tensile force treatment. Accordingly, the actuator may hang or otherwise be suspended from a region of appropriately tough or durable tissue (e.g., connective tissue fascia, chest wall) adjacent to the tissue region(s).

The covering(s) may be include any suitable material. In some embodiments, a covering includes an elastomeric material, such as a soft, biocompatible and waterproof layer of silicone elastomer (e.g., SILASTIC®). The covering(s) may also include any suitable polymer, for example, polyethylene terephthalate, polyester, polyvinyl chloride, polystyrene, polyethylene, polypropylene, polyacrylonitrile, polyvinyl butyral, silicone, etc. In some cases, the covering includes an embedded polyester mesh that provides the covering with an increased resistance to abrasion. The covering may incorporate other suitable materials, or combinations thereof.

Figure 5A:
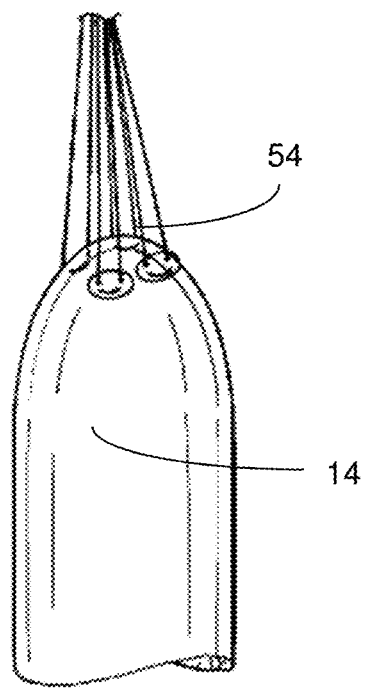
FIGS. 5a-5b show perspective views of the effect of using support members in accordance with an embodiment.

When using conventional techniques to apply tensile forces to certain tissue regions such as tissue conduits, undesirable necking or tapering of the region may occur. For example, the end of a tissue conduit where tensile forces are applied may be weakened, or may deform such that flow through the conduit may be restricted. Such occurrences may lead to additional surgery in the future. As an example illustratively shown in FIG. 5a, the suture 54 (e.g., pledgeted suture) is sewn into the end of the distal esophagus portion 14 and pulled so as to apply upward tensile forces thereto that are concentrated at the attachment points. Here, the tissue is stretched, however, there may be a risk of undesirable tearing or deformation associated with such an arrangement, particularly at the regions where the tensile forces are greatest.

Further, to form a fully functional biological passageway (e.g., esophagus), it may be insufficient to stretch the tissue conduit(s) only to the point where opposing ends (e.g., proximal and distal esophagus segments) meet. That is, it may be necessary for the tissue conduit(s) to be stretched so that there is a reasonable amount of overlap between the opposing ends, for a viable attachment to be formed therebetween. For instance, it may be more desirable for respective regions of tissue conduits that have not experienced the effects of tapering to be attached to one another, as tapered regions may be more prone to tearing, leakage, damage, etc. Accordingly, when a tissue conduit is sufficiently stretched, any tapered region(s) are removed so that the portion(s) of tissue that are not weakened are used for attachment of the previously separated segments. Thus, in some cases, support members may be attached to tissue regions an appreciable distance offset from the respective ends of the tissue (e.g., well above the proximal esophagus end, well below the distal esophagus end), so that when stretched such that the rings are moved to be adjacent each other, extra tissue is then available to join the two segments together. However, for instances where only a limited amount of tissue is available to begin with, the support members may be laterally offset with respect to one another, as discussed above.

By using support members in accordance with the present disclosure, less necking or tapering may occur at the respective tissue regions; hence, it may not be necessary for the support members to be attached to the tissue regions so far from the ends than would otherwise be the case. That is, attaching sutures directly to the end of a tissue conduit for stretching thereof, absent additional support structure, may lead to more stretching of tissue than would otherwise be required, or preferred, when using embodiments described herein.

In accordance with various embodiments, support members described herein may provide a tensile force that is substantially evenly distributed along the surface of tissue regions to which the support members are attached. When the tensile forces along the tissue region are well distributed, stretching or growth of the region may occur in a manner that maintains a desirable size and shape, hence, the chances of the suture(s) tearing through the tissue or stricture of the region is substantially reduced.

Figure 5B:
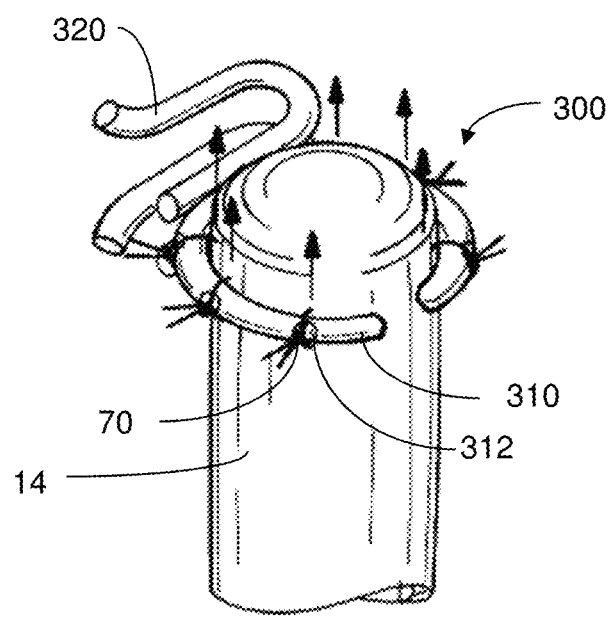

In the illustrative embodiment of FIG. 5b, the distal support member 300 is positioned such that the arcuate portion 310 of the ringed structure is placed around the distal esophagus portion 14. As shown, the arcuate portion 310 and the distal esophagus portion 14 are sutured together in a relatively even manner around the circumference of the tissue conduit. The sutures 70 are positioned and remain in place within respective recessed regions 312, which limit the ability for the sutures to slide around the surface of the arcuate portion 310. As the actuator 100 moves the distal support member 300 in an upward direction, the distal esophagus portion 14 is pulled along so as to cause stretching of the tissue. This stretching occurs via a substantially uniform distribution of tensile force along the circumference of the tissue conduit, as shown by the arrows in FIG. 5b.

This substantially uniform distribution of tensile force along the circumference of the tissue conduit results in stretching or growth of the conduit in a manner that preserves its diameter. As a result, any risk of tearing or stricture of tissue that would otherwise arise in the absence of the support member is significantly reduced.

In some cases, it may be preferable for the sutures to be sewn or coupled to a region of tissue that is relatively sturdy and resilient, so that the tissue does not neck or deform in an undesirable manner. Such tissue is generally located at the outermost region of the tissue region. Accordingly, during implantation, care may be taken for the sutures to avoid the innermost mucosa layer, which is relatively soft and may be prone to infection, particularly if the suture tears through.

The support members may include any suitable material or composition. In some embodiments, the support members may be relatively rigid so as to provide a sufficient degree of support for attachment of the sutures to the tissue region. For example, the support members may be composed of biocompatible stainless steel, or other suitable materials. In some embodiments, the support members may exhibit an appropriate ability to deform, allowing a user, during the implantation procedure, to adjust the diameter or shape of the support member (e.g., arcuate portion) to that which physically conforms to or otherwise complements the shape of the tissue region (e.g., esophagus, bowel). In some cases, the support member(s) may be made from a resorbable material. As a result, the support member(s) may be left in place after implantation without removal thereof. Or, when treating esophageal atresia, during anastomosis, the support members may be attached together to maintain the relative position between opposing tissue conduits.

Figure 5C:
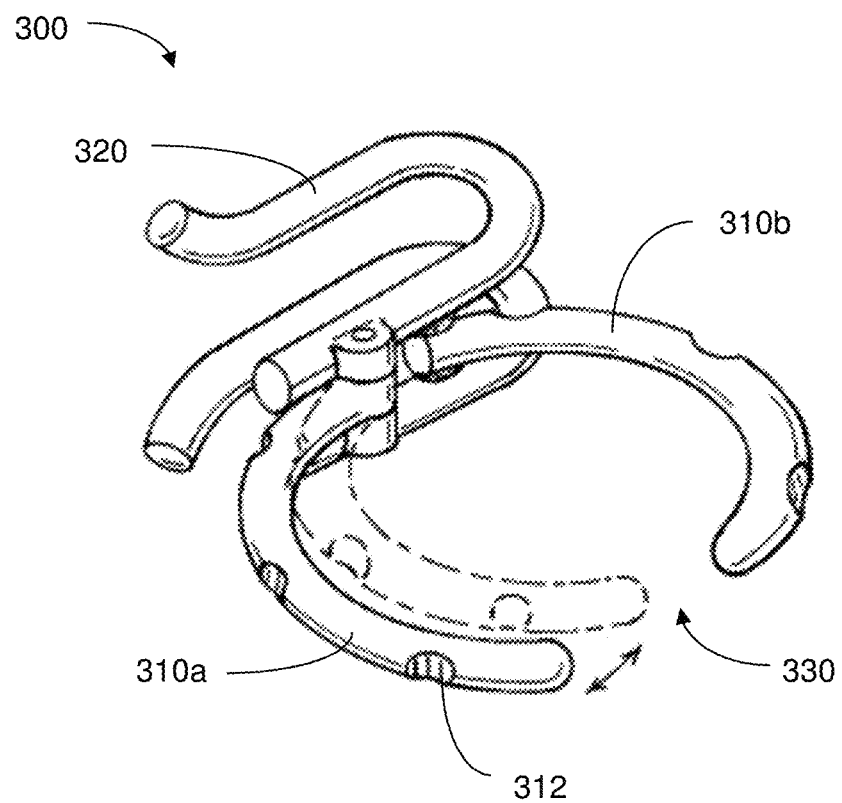
FIG. 5c depicts a support member in accordance with an embodiment.

The support members may be adjustable in size and/or shape to suit the tissue region to which the support members are attached. For example, FIG. 5c shows an illustrative embodiment of a support member 300 where a first arcuate portion 310a and a second arcuate portion 310b are provided in a hinged arrangement. Accordingly, when the first and second arcuate portions 310a, 310b are moved apart from one another, the support member 300 may accommodate entry of an appropriately sized (e.g., relatively large) tissue conduit. Conversely, moving the first and second arcuate portions 310a, 310b toward one another may provide for a tighter fit between the support member 300 and the tissue conduit. That is, when installing the support member 300, the arcuate portions 310a, 310b may be moved apart so that the tissue conduit may enter into the area defined by the ring. When attaching the support member 300 to the tissue conduit, the arcuate portions 310a, 310b may be moved toward one another so that the tissue conduit is suitably supported. It can be appreciated that other arrangements for adjusting the size and/or shape of a support member may be possible.

It should be appreciated that the present disclosure is not limited to the particular manner in which the actuator causes movement of the support members (e.g., suture rings) back and forth. That is, the actuator may function according to any suitable mechanism to move the support members. In some embodiments, the actuator may be configured to move one of the proximal or distal support members back and forth (e.g., along an axial direction of the esophagus) while keeping the other support member relatively stationary. For instance, as shown for some embodiments presented herein, the actuator may be arranged as a rack and pinion where one of the support members remains fixed while the other support member moves up and down the rack.

Or, in some embodiments, the actuator may be configured to control movement of both the proximal and distal support members, together or separately. That is, movement of the proximal and distal support members may be independently controlled to stretch the tissue region in any suitable direction (e.g., along an axial direction). Or, the support members may be coupled in an appropriate manner so as to provide the tissue with a suitable pattern of tensile force treatment.

The manner in which tensile force is applied to the tissue regions(s) may also vary to be continuous or non-continuous. For instance, after a desired tensile force is applied to a tissue region for a certain interval, it may be preferable for the support member to be held in position for a different period of time until a subsequent tensile force adjustment is desired. In some embodiments, the tensile force(s) may be applied in short time bursts (e.g., 1-2 minutes). Or, it may be preferable for the actuator to move the support member(s) so as to exert a relatively constant tensile force on the tissue region(s) over a long period of time (e.g., approximately a day).

Accordingly, depending on the particular characteristics of the tissue, and aspects of the condition to be treated, the pattern in which tensile force is applied may vary appropriately. In some embodiments, the tensile force(s) applied to the tissue region(s) may be increased incrementally once per day and then, after a certain period, the tissue may be allowed to relax. For example, the tensile force(s) may be applied daily for a period of one or two minutes (e.g., continuous or periodic pattern) over the course of approximately one month. Or, the actuator may be configured to cause a particular amount of elongation of the tissue region (s) per day (e.g., approximately 1.0 mm per day, approximately 5.0 mm per day).

The displacement of support member(s) and tissue region (s) and the resulting tensile force(s) applied to the tissue region(s) may be appropriately monitored and controlled. The ability to monitor and control these values may allow medical personnel to tailor the force(s) applied by the actuator to the particular tissue structure. For example, if the tissue region(s) are relatively weak, then the respective tensile force(s) applied thereto may be correspondingly short, gradual and low in force. Though, if the tissue region(s) exhibit a high degree of strength, then a relatively greater amount of tensile force(s) may be applied over a given interval, so as to shorten the overall period of the entire treatment. Or, the amount of force applied to the tissue region(s) may be greater or less depending on the stage of treatment. For example, in the case of treating esophageal atresia, the amount of force applied upon initiating treatment may be greater than the amount of force applied further along during treatment or near the end of treatment, or vice versa.

In some embodiments, using systems described herein, the tensile force applied to a tissue region at a particular time may be greater than 0.1 N, greater than 0.5 N, greater than 1.0 N, greater than 2.0 N, greater than 3.0 N, greater than 4.0 N, greater than 5.0 N, greater than 8.0 N, or greater than 10.0 N. Or, the tensile force applied to a tissue region at a particular time may be less than 10.0 N, less than 8.0 N, less than 5.0 N, less than 4.0 N, less than 3.0 N, less than 2.0 N, less than 1.0 N, less than 0.5 N, or less than 0.1 N. Combinations of the above-referenced ranges are also possible. Or, other values of tensile force applied to tissue regions are possible for certain instances.

In some embodiments, with force and displacement sensors incorporated therein, a controller may be employed with a suitable interface for controlling the actuator to move the support member(s) in a precise manner so as to regulate the force applied to and/or displacement exhibited by the tissue region(s). For example, a support member may be driven by the actuator to apply a therapeutic tensile force to a corresponding tissue region up to a specified set point and then the corresponding position may be held while monitoring force and position over time. Accordingly, in such a case, the motor may be activated during set point force control, and the transmission associated with the motor may be used to hold the gap distance between support members fixed between actuation cycles.

In some embodiments, the controller may be programmed to apply a therapeutic tensile force that corresponds to a tissue lengthening procedure that substantially replicates current clinical practice. In such instances, the amount and degree of X-ray monitoring, and the radiative treatments associated therewith, may be reduced.

As shown in various embodiments, cables may exit the chest cavity so as to be in electrical communication with a power source and/or controller that is used for continuous monitoring and regulation of the applied tensile force and/or gap size between tissue regions. In some embodiments, the implantable apparatus may be wireless. That is, upon implantation, the body cavity would be completely closed, without any need for a cable or other communications line to physically extend from the body of the patient.

Figure 6A:
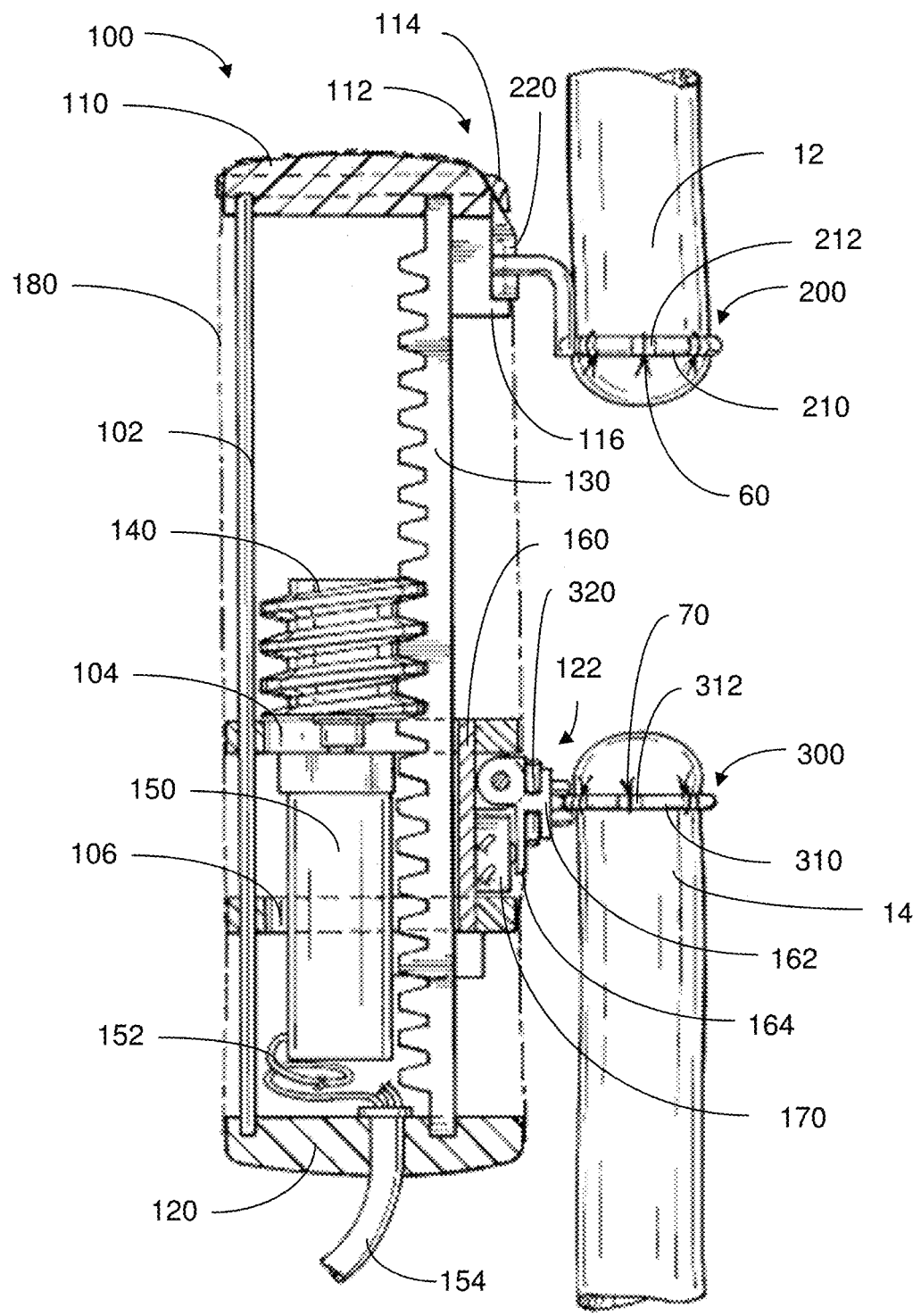
FIGS. 6a-6c depict an implantable apparatus in use in accordance with an embodiment.

FIG. 6a depicts an illustrative embodiment where a proximal support member 200 is attached to a proximal esophagus portion 12 via sutures 60. The sutures 60 are positioned within recessed regions 212 spaced along the circumference of the arcuate portion 210 (shown as a suture ring) of the support member 200. The proximal support member 200 is, in turn, coupled to the actuator 100 via attachment of the proximal coupling portion 220 to the anchor portion 112 of the actuator.

Similarly, sutures 70, positioned within recessed regions 312 located along the circumference of the arcuate portion 310 (shown as a suture ring of the distal support member 300), are used to attach the distal support member 300 to a distal esophagus portion 14. The distal support member 300 is further coupled to the actuator 100 through attachment of the distal coupling portion 320 to the anchor portion 122 of the actuator.

Figure 6B:
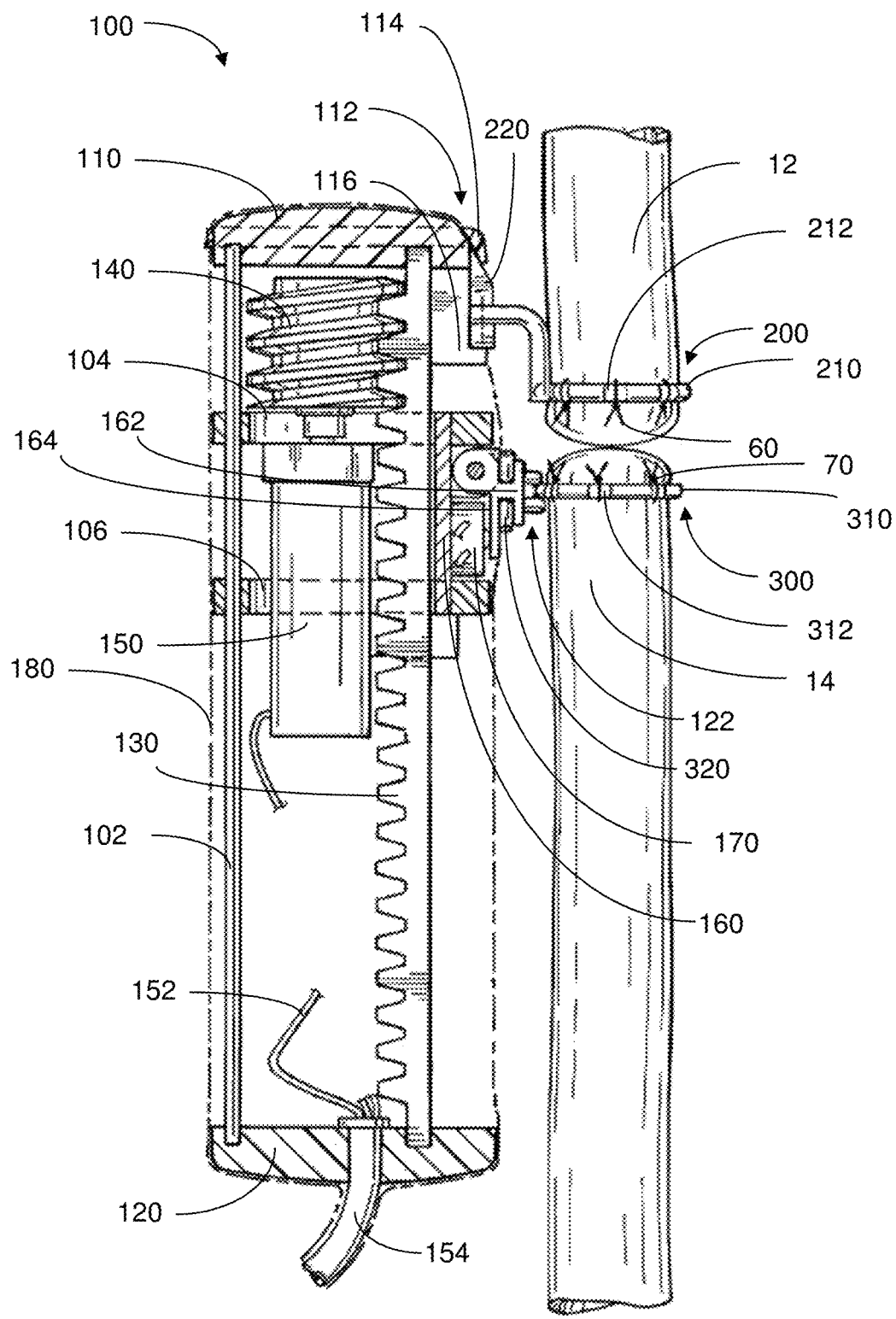

After a suitable pattern of therapeutic tensile forces are applied to the esophageal segments, a follow up surgery is performed. During the surgery, the ends of the pouches of tissue are cut so as to expose the respective passageways of each tissue segment. The opposing esophageal segments are then joined together. For example, FIG. 6b shows the embodiment of FIG. 6a where the actuator 100, coupled with proximal and distal support members 200, 300, has stretched the proximal and distal esophagus portions 12, 14 sufficiently so that the tissue is ready for anastomosis. At this point, for some embodiments, to make room for anastomosis, various implanted components of the apparatus are removed prior to attaching the tissue conduits together. For example, the entire apparatus may be removed from the body. Or, the actuator portion of the apparatus may be removed while the support members remain to hold the esophageal segments in apposition to facilitate anastomosis. After the pouches are cut and the ends of the respective esophagus portions 12, 14 are appropriately aligned, the segments are sewn together via sutures 80, to form a suitable passageway between the pharynx and the stomach.

Figure 6C:
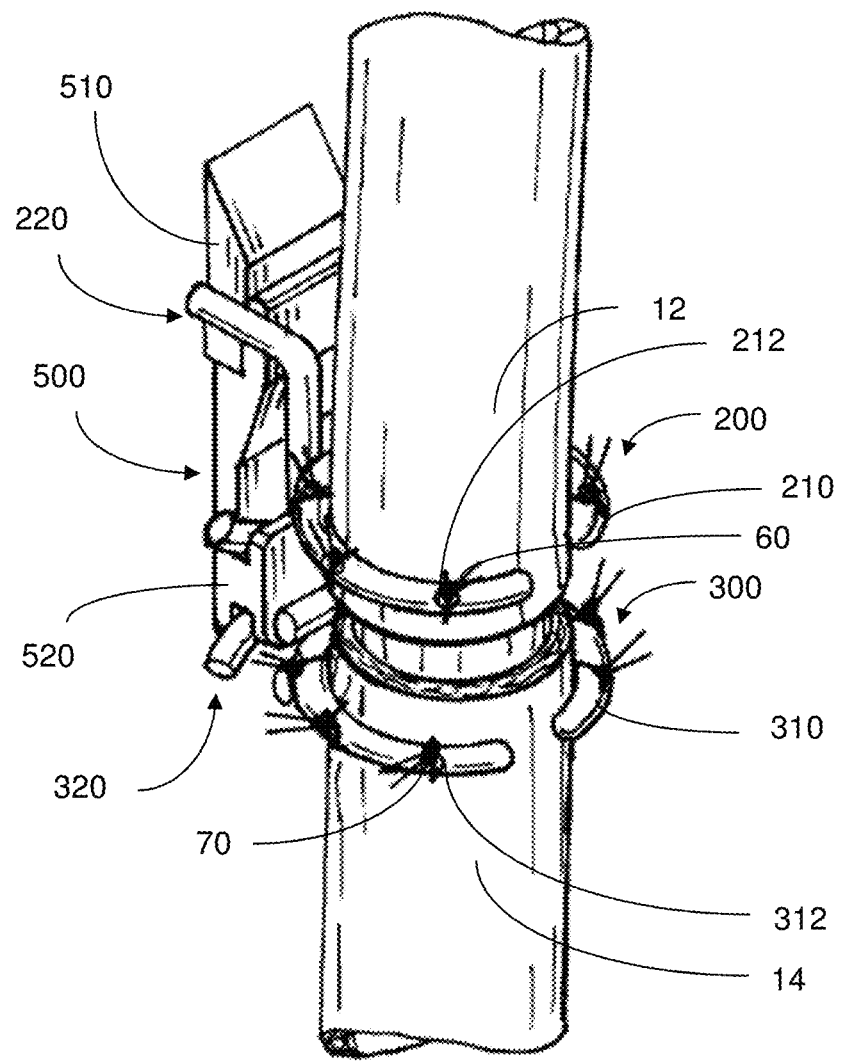

As noted above, the actuator may be removed from the body while the support members the esophageal segments in place for attachment therebetween. In some embodiments, a connecting component or clip may be attached to each support member to hold them fixed with respect to each other. For example, FIG. 6c depicts an illustrative embodiment of such a connecting component 500. The connecting component 500 has a proximal connecting portion 510 and a distal connecting portion 520. As shown in FIG. 6c, the respective connecting portions 510, 520 have structure analogous to that of the anchor portions 112, 122 of the actuator 100, complementary to the corresponding coupling portions 220, 320 of the support members 200, 300. Accordingly, the actuator 100 is effectively replaced with the connecting component 500, which is comparatively smaller, yet provides sufficient structure to hold the support members 200, 300 in place during anastomosis.

In some embodiments, such connecting component(s) may be built into the support members 200, 300. That is, the support members may be designed to connect to each other upon approach.

As noted above, upon completion of the follow up surgical procedure (e.g., after anastomosis) where the actuator is removed, the support member(s) may be left in place. For example, the support member(s) may be resorbable. In some cases, leaving the support member(s) at the site of actuation may be beneficial in that it may prevent the formation of strictures that would otherwise arise at the site of anastomosis.

An illustrative embodiment of a procedure for treating long gap esophageal atresia employing aspects of the present disclosure will now be described.

As a first step, a right-sided thoracotomy is performed. A thoracotomy involves a surgical incision into the pleural space of the chest for gaining access to the thoracic organs, in this case, the esophagus. The lung is gently retracted medially, providing suitable exposure of the esophagus segments.

At this point, any undesirable fistulas, such as tracheoesophageal fistulas, are surgically removed. Tracheoesophageal fistulas are commonly observed along with esophageal atresia and are characterized by an abnormal connection between the trachea and esophagus. Because the respective passageways for air (i.e., trachea) and food (i.e., esophagus) are to be kept separate, tracheoesophageal fistulas should be repaired prior to tensile force treatment.

In this embodiment, while not required, the suture rings are initially provided detached from the actuator. Depending on the respective sizes (e.g., diameter) of the proximal and distal esophagus portions, the suture rings may be selected from a group of possible suture rings having an assortment of sizes. Or alternatively, as discussed above, the suture rings themselves may be adjustable in diameter such that the appropriate medical personnel may be able to shape the suture rings appropriately to fit around the respective esophagus portions. As also discussed above, selecting the size of the suture rings to complement the corresponding esophageal diameters may be effective to induce suitable tubular growth rather than, for example, necking or narrowing that may otherwise arise without the rings or other appropriate support member. Accordingly, the treatment may result in greater lengths of useable tissue (e.g., less tissue wasted) for anastomosis as well as an overall reduction in strictures.

Once the suture rings are ready for attachment, the proximal esophagus portion is slipped into the proximal suture ring and the distal esophagus portion is slipped into the distal suture ring. The proximal esophagus portion and the proximal suture ring are then sutured together along their circumference. Similarly, the distal esophagus portion and the distal suture ring are also sutured together along their circumference. The sutures are relatively evenly distributed along the circumference of the suture rings and esophagus portions.

In some cases, as noted above, the suture rings may be imaged so that medical personnel are able to know their position within the body during implantation. In addition, radioactively traceable markers (e.g., for x-ray imaging) may also be attached to the proximal and distal esophagus portions.

Once the suture rings are suitably secured to the respective esophageal segments, the rings are then coupled to the actuator. That is, the proximal suture ring is coupled to a proximal anchor portion of the actuator and the distal suture ring is coupled to a distal anchor portion of the actuator.

A sheet of elastomeric silicone may be wrapped around both the separated esophageal segments and implanted apparatus, and subsequently attached to the chest wall. As a result, the sheet of elastomeric silicone provides a hammock-type arrangement where the esophageal segments and implanted apparatus are able to hang or otherwise be supported by the chest wall, while not causing adverse effect(s) to the tensile force treatment.

A tunnel may be formed within the subcutaneous tissue for actuators that are connected by a cable to electrical or mechanical components (e.g., power source, controller, motor mechanism, etc.) that are located outside of the body. The tunnel may extend from any suitable portion of the actuator. For example, as shown in several of the figures, since the cable extends from the distal end of the actuator, the tunnel may be formed at the distal end so as to accommodate cable connection(s) between the implanted apparatus and the appropriate component(s) in a sterile manner. In some embodiments, the size (e.g., diameter) of the cable connector(s) may be as small as or otherwise may approximate the size of the corresponding cable(s), allowing for the connector to pass through a relatively small incision within the skin. Or, alternatively, for arrangements where the actuator is in wireless communication with the controller or power source, it might not be necessary for a separate tunnel within subcutaneous tissue to be formed. Accordingly, the actuator itself may have a microprocessor, which may enable wireless communication with a microprocessor of the controller.

In an embodiment, the microprocessor of the implantable actuator sends control signals to the motor, for example, based on various sensor signals, so as to impart force and/or motion to the anchor portion(s). This microprocessor may also stream sensor data back to another microprocessor, located remotely from the implantable apparatus. The remote microprocessor may be used to store, process and/or plot data and to convey high-level control commands to the device controller. A high-level command might be, for example, to change the amplitude of force oscillation, or another appropriate adjustment in treatment. It can be appreciated that control of the actuator and corresponding components may be distributed between multiple microprocessors in any suitable manner.

Once the various components of the apparatus are suitably coupled to the tissue (e.g., surrounding tissue and tissue region(s)) and to each other (e.g., suture rings coupled to the actuator, actuator in communication with the power source and controller), the implanted apparatus is tested for appropriate functionality. That is, the operator may verify that the applied force(s) and strain(s) on the tissue region(s) are provided within normal operating parameters. For example, an initial tensile force may be applied during surgery to test the system. Once this verification is complete, the open surgical cavity (e.g., chest, abdomen) is closed.

Once the patient is revived from anesthesia, therapeutic traction force treatment may be applied. As a result, medical personnel may be able to distinguish between pain arising from surgery versus pain arising from excessive tensile forces. In some cases, during treatment, pain medications may be used to enable higher tensile forces to be applied.

Tensile force(s) and displacement(s) of the esophageal segments are applied and monitored continuously. In some embodiments, tensile forces are adjusted in a periodic fashion. For example, in accordance with current practice using the Foker technique, and as noted above, the force may be increased once per day. Or, tensile forces may be applied cyclically with a gradual decrease in force throughout the day. As also described herein, the pattern of force treatment may appropriately vary depending on the patient. Because the patient does not need to be paralyzed and sedated during application of tensile forces, the level of force that can be tolerated by the patient will also be determined.

Radiative imaging (e.g., X-ray analysis) may be performed regularly so as to verify the performance of the implanted apparatus. By regular monitoring and imaging, medical personnel may be able to determine whether the conditions are suitable for anastomosis. That is, once the suture rings are moved together as desired and the measured tensile force applied to the tissue is significantly reduced to a suitable degree, an additional surgery will be performed to remove the implanted materials, cut off the esophageal pouches together with the rings and perform an anastomosis to join the two segments.

As further discussed herein, in the case of treating esophageal atresia, simply stretching or growing the tissue regions to respective lengths long enough for the proximal and distal esophagus portions to be joined may be insufficient for a healthy esophagus to ultimately result. For instance, it may be preferable for a sufficient amount of overlap between portions of the segments to occur before anastomosis so that healthy segments of tissue are joined together. As an example, the two esophageal ends may be pulled together, cut in an appropriate manner and joined. Or, the two esophageal ends may be pulled side by side at an offset to create an overlapping length therebetween. Once a suitable amount of overlap is created, the segments are cut and joined.

In some cases, as the junction heals, there may be a tendency for the passageway to constrict. Accordingly, an additional procedure may be performed that enlarges the passageway at any particular point(s) of stricture. For example, a balloon catheter may be guided into the region where stricture has occurred, or is at risk of occurring, and is appropriately enlarged, however many times as desired.

As noted herein, conventional techniques for treating long gap esophageal atresia, such as the Foker method, typically require the patient to be kept in the hospital for approximately 3.5 months. Though, using techniques described herein, the patient may be kept in the hospital for 1 month or less, significantly reducing risks of patient morbidity.

As also discussed above, aspects of the present disclosure are applicable to other medical conditions where the application of tensile forces to stretch or grow one or more tissue regions may be desirable. For instance, an actuator and/or support members in accordance with embodiments described may be used to treat short bowel syndrome. In such a case, a support member may be attached to a shortened intestine and the actuator may cause movement of the support member in any suitable direction, resulting in stretching or growing of the bowel. In some embodiments, two support members (e.g., suture rings) are attached to the bowel and are moved apart from one another to stretch the bowel.

In various embodiments described herein, an actuator is implanted within a body cavity directly adjacent to the tissue region(s) to be treated. It may be preferable for the space occupied by the actuator be minimal. That is, in some cases, the actuator and associated support members may take up relatively little space. For example, in some embodiments, for a motor-powered actuator, the motor may remain outside of the body during tensile force treatment. Or, alternatively, as discussed below, the actuating element(s) of the actuator may be substantially aligned with the support member(s) and the tissue region(s).

Figure 7:
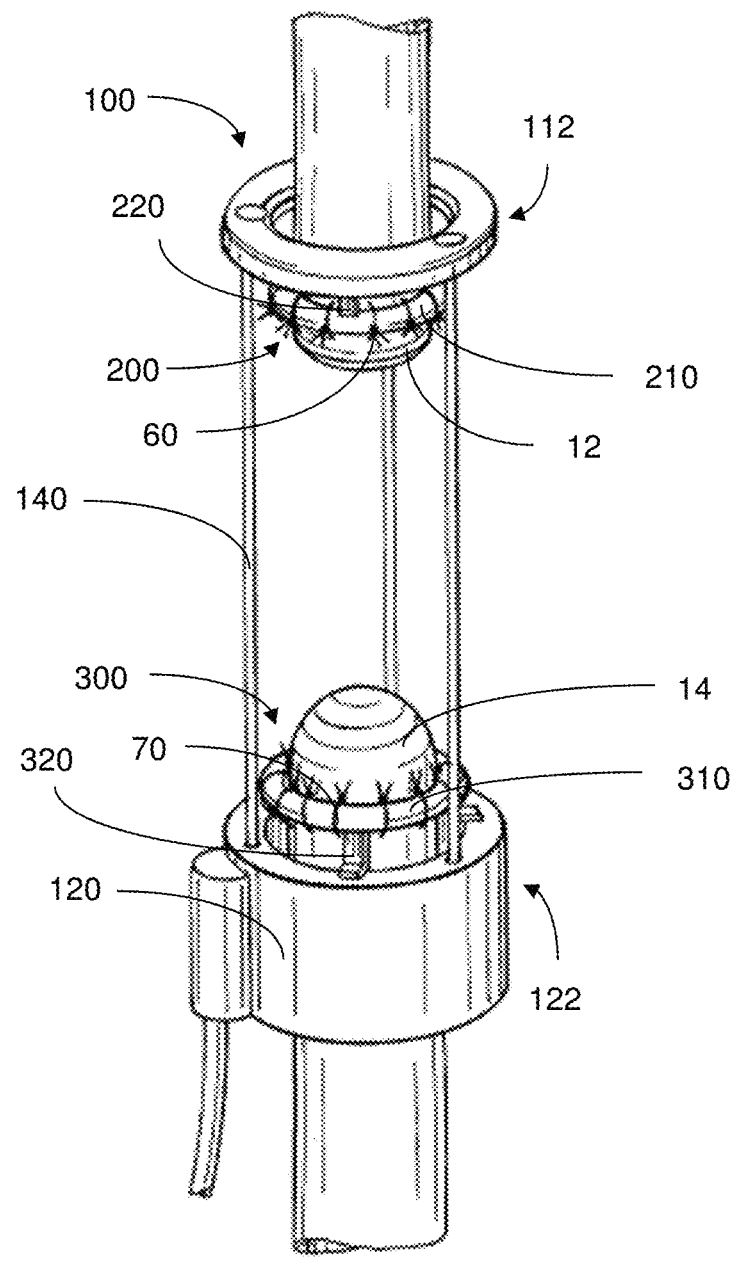
FIG. 7 illustrates a perspective view of an implantable apparatus in use in accordance with an embodiment.

FIG. 7 depicts an illustrative embodiment of an implantable apparatus where the actuator 100, the support members 200, 300 and the tissue regions 12, 14 are arranged in a substantially aligned configuration. Here, similar to other embodiments described, the proximal support member 200 is sutured to the proximal esophagus portion 12 and the distal support member 300 is sutured to the distal esophagus portion 14. Though, rather than the anchor portions 112, 122 of the actuator 100 being laterally offset from the support members, in this embodiment, the anchor portions 112, 122 are substantially aligned with the support members. As shown, the support members 200, 300 are coupled to the respective anchor portions 112, 122 via coupling portions 220, 320.

The coupling portions 220, 320 may include any appropriate complementary coupling structure for attaching the support members 200, 300 to the anchor portions 112, 122 (e.g., snap-fit, press-fit, slot connection, etc.). While not shown, the apparatus may incorporate force and/or displacement sensors, for example, positioned at the support member(s) and/or anchor portion(s) of the actuator. As a result, such arrangements may take up a relatively small amount of space within the chest cavity.

As further shown in FIG. 7, the actuator 100 includes actuating elements 140 extending between the proximal anchor portion 112 and the distal anchor portion 122. In this embodiment, the actuating elements 140 are provided as flexible components, such as suture thread (e.g., polypropylene), cable, or other string-type material, that are tensioned so as to pull the anchor portions 112, 122 together.

Any suitable manner may be used to impart tension to the actuating elements 140, or thread. In some embodiments, a motor (e.g., torsional cable drive, not shown in FIG. 7) may be configured to wind the thread around a spool or pulley (also not shown in FIG. 7). The motor, spool or pulley may be located at any appropriate location, such as within an anchor portion (e.g., proximal anchor portion 112, distal anchor portion 122) or apart from the actuator 100 (e.g., outside of the body cavity).

For example, in an embodiment, a spool may be located within an annular inner compartment of the distal anchor portion 114 of the actuator. The motor may be located within the distal anchor portion, or away from the actuator, and may be configured to cause winding of the thread around the spool. As the motor winds the thread around the spool, the tension in the thread is increased. As the tension in the thread increases, the proximal and distal anchor portions 112, 122 are drawn toward one another. Such movement also brings the proximal and distal support members 200, 300 toward one another which, in turn, imparts tensile force to the respective esophageal segments.

As noted above, for some embodiments, the motor, or other appropriate device for driving mechanical motion, may be located remotely from the actuator, such as at another part of the body (e.g., abdomen), or external to the body. Because there is little space in the chest cavity adjacent to the esophagus, it may be preferable for the motor to be located away from the actuator.

As also noted above, the support member may be attached to the inside of the tissue conduit(s). For example, in another embodiment, an internal version of the system shown in FIG. 7 (not shown in the figures) may be employed. Accordingly, when treating esophageal atresia, the support members (e.g., suture rings) may be placed inside the tissue conduit and one or more actuating elements (e.g., sutures) may be arranged so as to exit the proximal esophageal pouch and enters the distal esophageal pouch. In addition, various portions of the device may be located in the stomach and electrical/transmission cables may further be arranged to parallel a feeding tube that enters the stomach.

Figures 8A, 8B:
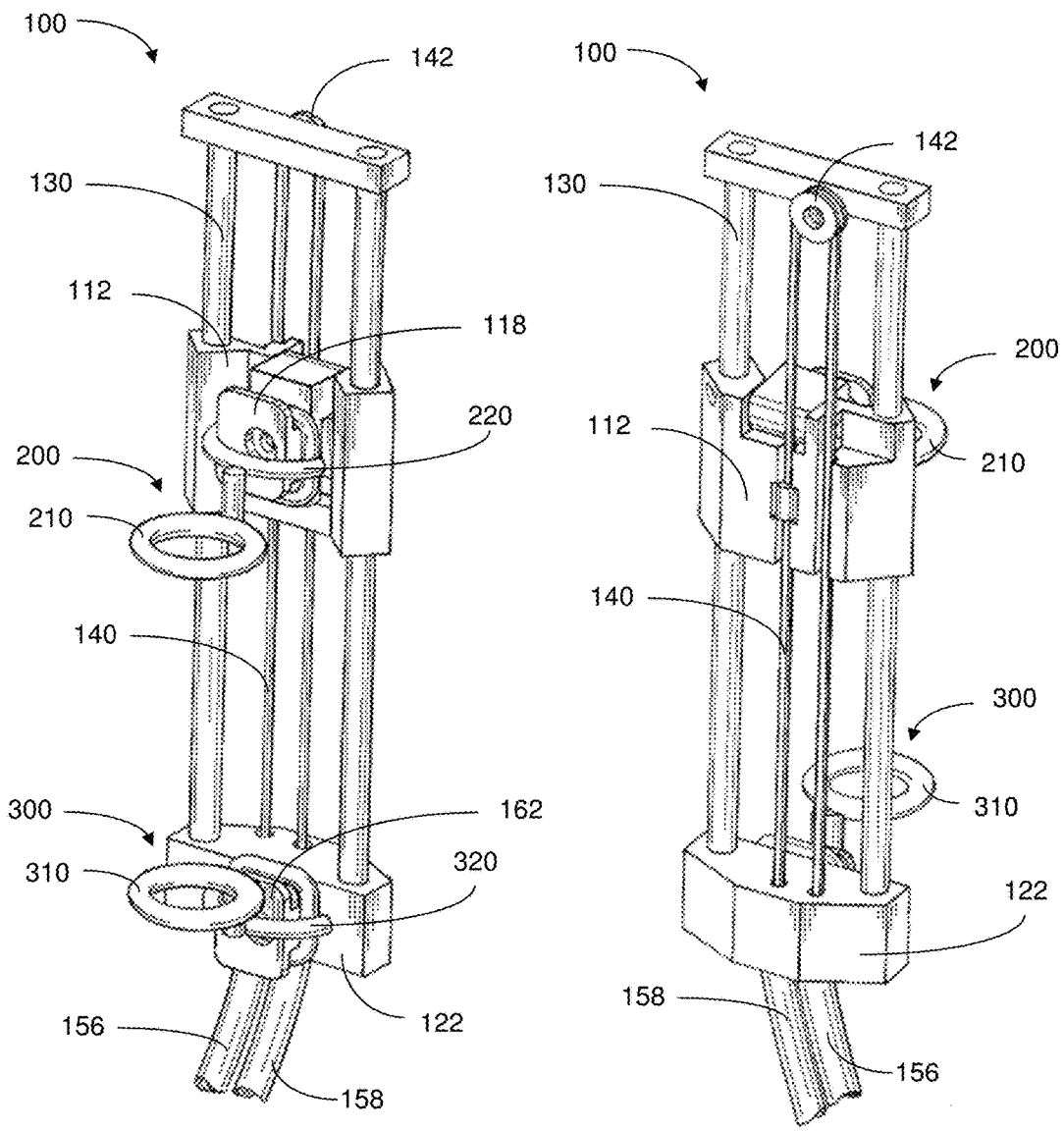
FIGS. 8a-8b depict perspective views of another implantable apparatus in accordance with an embodiment.

FIGS. 8a and 8b depict another illustrative embodiment of an apparatus including an actuator 100 having a proximal anchor portion 112 and a distal anchor portion 122 that are configured to move along a track 110 upon winding and unwinding of an actuating element 140, provided in this embodiment as a suture thread, around a pulley 142. The thread extends away from the main body of the actuator 100 to the motor (not shown in FIGS. 8a and 8b) via cables 156, 158. In this embodiment, the motor is located remotely from the actuator, away from the esophagus.

As shown, a proximal support member 200 having an arcuate portion 210 (e.g., suture ring) and a coupling portion 220 is attached to the proximal anchor portion 112 of the actuator 100. Here, the coupling portion 220 is structured so as to be wrapped around a complementary plate 118. Similarly, a distal support member 300 having an arcuate portion 310 and a coupling portion 320 is attached to the distal anchor portion 122 of the actuator.

When the support members 200, 300 are suitably attached to the appropriate tissue regions, the support members are then coupled to the respective anchor portions 112, 122 of the actuator 100. Subsequently, during operation, the motor winds the thread so as to impart tension thereto. As tension builds up, the thread is pulled over and around the pulley 142, causing relative movement of the anchor portions 112, 122 toward one another. Accordingly, based on the degree to which the thread is pulled, anchor portions are drawn toward one another so as to impart appropriate tensile force(s) to the tissue region(s). In this embodiment, the motor, or other device that powers the actuator, may be advantageously be located remotely from the site of implantation.

In some embodiments, during tensile force treatment of esophageal atresia, despite the gap that still remains between opposing tissue regions, it may be desirable for food or liquid content to be able to travel between the pharynx and the stomach. Accordingly, an artificial tube may be provided as a temporary passageway between the disconnected segments. Such tubes may maintain a suitable connection between the proximal and distal esophagus portions during tensile force treatment. That is, the tube may provide a passageway for food or liquid travel between tissue segments at the beginning of treatment, when the esophagus portions are further away from one another, and also at the end of treatment, when the esophagus portions are in close proximity to one another. Accordingly, even if the tube encounters substantial changes in length (e.g., shortening), the tube may still provide a suitable passageway between the segments.

Various embodiments of tubes used for feeding may be employed. For example, such tubes may be made up of elastic biocompatible material, or another suitable material.

Figure 9A:
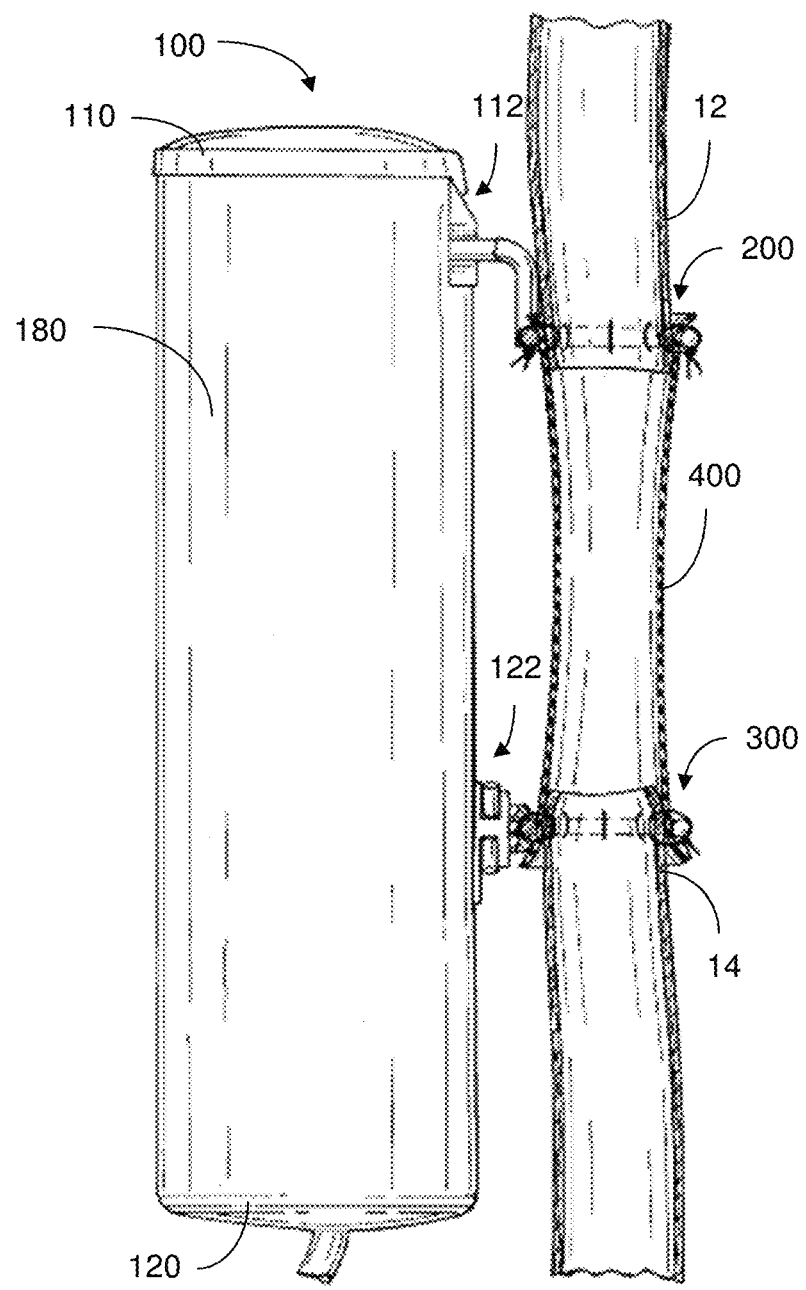
FIGS. 9a-9b show plan views of a feed tube in use with an implantable apparatus in accordance with an embodiment.
Figure 9B:
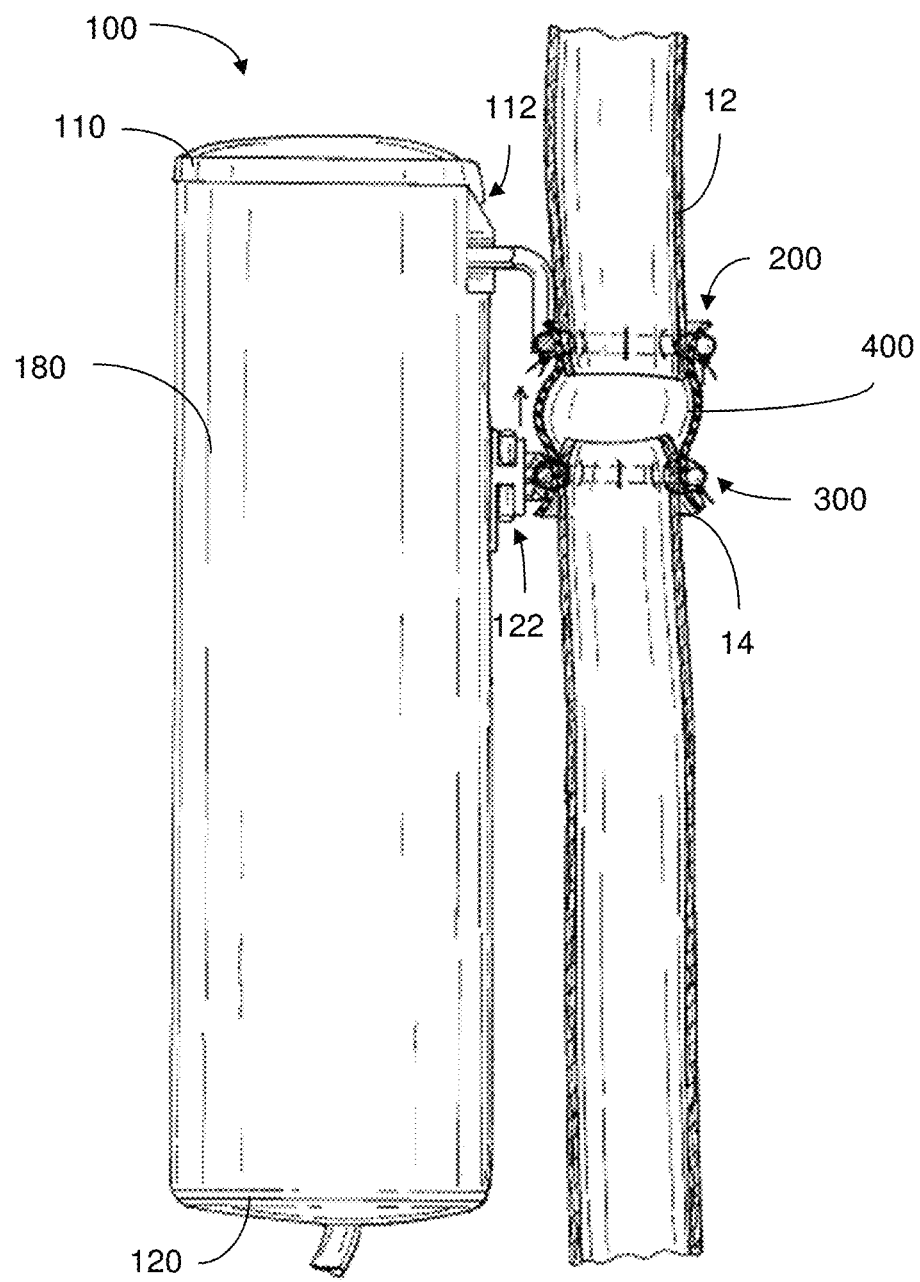

FIGS. 9a and 9b illustrate an embodiment where the proximal and distal esophagus portions 12, 14 are initially separate, yet a tube 400 (e.g., elastic tube) is provided therebetween. Accordingly, the patient may ingest food during tensile force treatment.

The additional tube may be installed with the opposing tissue conduits by any suitable technique. The pouches of the proximal and distal esophagus portions may be cut and the tube may be attached to respective openings thereof. In some embodiments, a suitable adhesive is used to attach ends of the tube to respective esophagus portions. Or, temporary sutures may be used to stitch ends of the tube to corresponding esophagus portions.

FIG. 9a illustrates the substantial gap that is present between the proximal and distal esophagus portions 12, 14 prior to or at the initial stages of treatment. FIG. 9b depicts the proximal and distal esophagus portions 12, 14 at a later stage of treatment where the ends are brought closer together. The tube 400 still remains between the two esophagus portions 12, 14 and, in some cases, bulges radially outward as the tissue segments approach one another. When the opposing tissue segments are close enough for anastomosis, the tube 400 is removed and the segments are sutured together.

Figure 10:
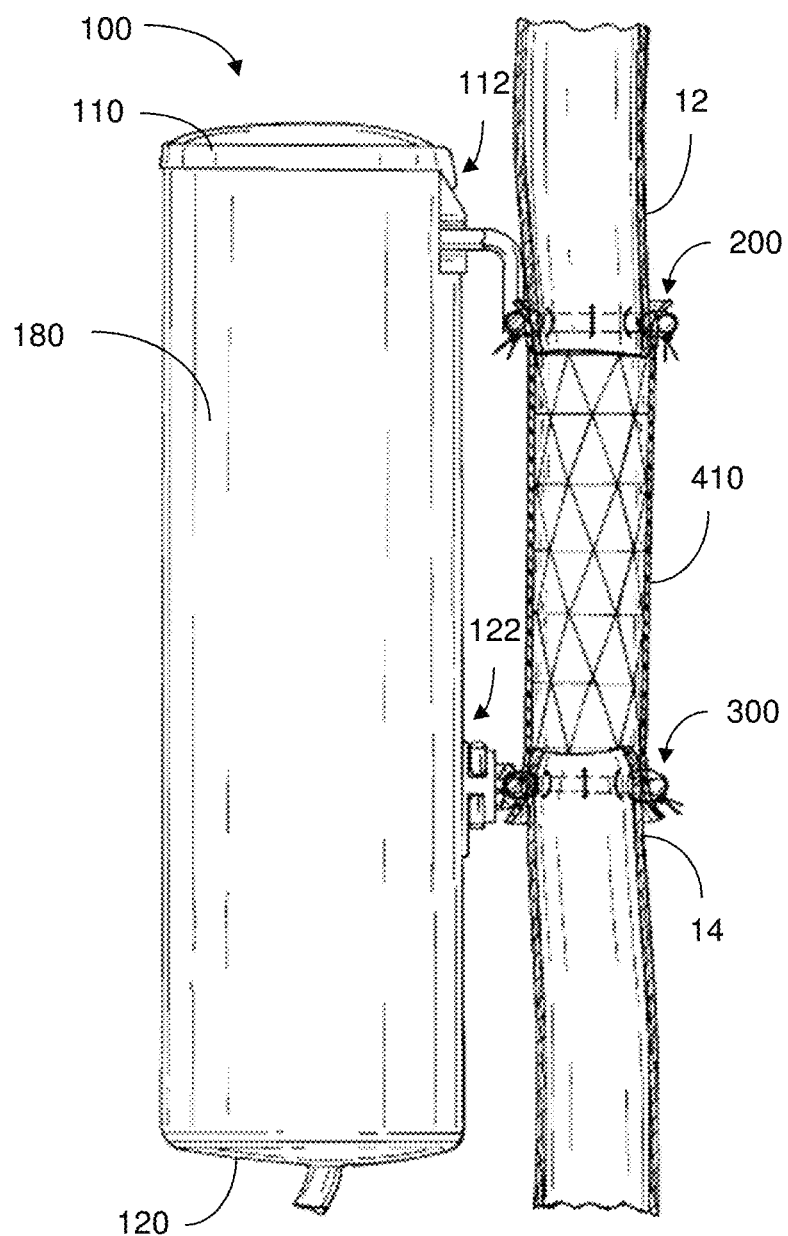
FIG. 10 illustrates another feed tube in use with an implantable apparatus in accordance with an embodiment.

FIG. 10 depicts an illustrative embodiment of a tube 410 having an origami composite configuration. Origami composite materials are known in the art and described in the article by Martinez et al., entitled "Elastomeric Origami: Programmable Paper-Elastomer Composites as Pneumatic Actuators," Advanced Functional Materials (22), 2012, relevant portions of which may be employed in various embodiments of the present disclosure. For example, such materials may be used to prevent the additional tube from buckling when compressed, so as to provide for a continuous passageway through which food and liquids may travel.

The tube 410 is positioned between proximal and distal esophagus portions 12, 14. As noted above, this tube 410 is able to fold in a manner that preserves the lumen of the region despite substantial shortening of the tube. Accordingly, food and liquids are able to pass from the pharynx to the stomach unhindered throughout tensile force treatment on the esophageal segments.

Figure 11:
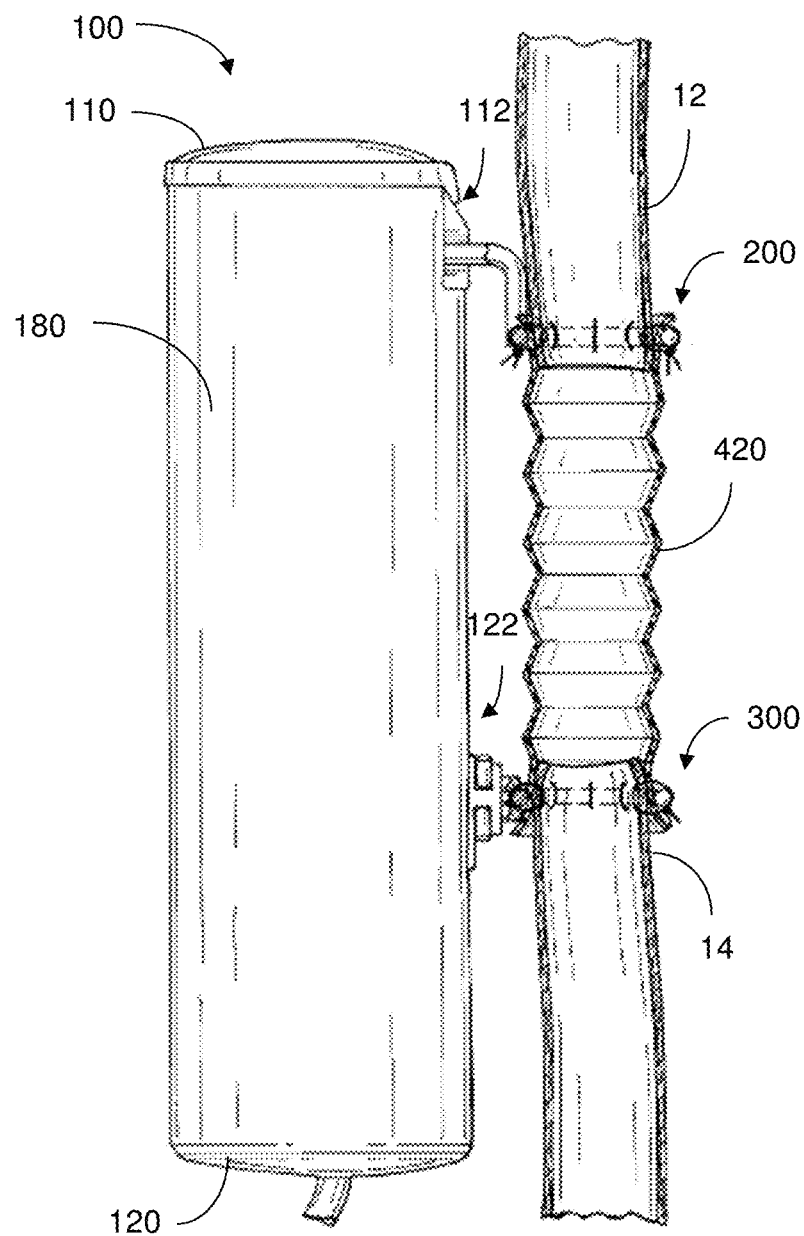
FIG. 11 depicts another feed tube in use with an implantable apparatus in accordance with an embodiment.

FIG. 11 shows another illustrative embodiment of a tube 420 having a bellows-type configuration. Here, similar to other embodiments, the tube 420 is able to maintain a suitable passageway for flow therethrough amidst shortening of the tube. When the proximal and distal esophagus portions 12, 14 are brought closer together, the tube 420 folds in a manner similar to an accordion so as to accommodate gap shrinkage between the segments.

In an example provided in accordance with the present disclosure, an actuator similar to the embodiment depicted in FIGS. 9a-9b was implanted via a right thoracotomy at an esophagus within a porcine model and tested in vivo over a 12-day period. The support rings were attached to the esophagus tissue, with titanium clips placed above and below the support rings so as to designate control tissue distances. The actuator portion was attached to the rings and a layer of SILASTIC was placed around both the actuator and the esophagus to provide a suitable level of isolation from the adjacent lung. The incision was closed with the cable from the implant tunneled out of the body through the skin to a control box located exterior to the animal. To allow the animal to recover from surgery, traction forces were not applied to the esophagus tissue until two days after implantation. Traction to the esophagus was increased by 2-3 mm each day.

The relative ring position and force were monitored using sensors built in to the actuator. Such information was stored real-time throughout the experiment. When the actuator was first implanted, the ring-to-ring distance was measured to be approximately 26 mm and the force between rings was measured to be approximately 0.16 N. On the final day of the experiment, the ring-to-ring distance was measured to be approximately 47 mm and the force between rings was measured to be approximately 1.7 N. The ring-to-ring distance was then reduced to a relaxed length where the force between rings was minimal, approximately 0.2 N. This relaxed length was measured to be approximately 37.9 mm. Hence, the resulting increase in esophageal growth was approximately 46%.

Fluoroscopic and X-ray imaging demonstrated that the esophageal tissue was patent for the entire period of implantation. Upon further examination, it was observed that the mucosal inner layer of the stretched esophagus appeared uniform and that the overall diameter of the esophagus, as measured by the width of the tissue, was approximately the same between the rings (where traction forces were applied) as in the region surrounding the rings (where no traction forces were applied). Such a finding suggests that use of the ring structure provides for a relatively uniform traction force applied to the circumference of the tissue, with a low probability that the esophageal diameter will be reduced.

Having thus described several aspects of at least one embodiment of this invention, it is to be appreciated various alterations, modifications, and improvements will readily occur to those skilled in the art. For example, the devices described herein may be adapted for use in medical or non-medically related applications. Such alterations, modifications, and improvements are intended to be part of this disclosure, and are intended to be within the spirit and scope of the invention. Accordingly, the foregoing description and drawings are by way of example only.

What is claimed is:

1. An implantable apparatus for applying force to bodily tissue, comprising:
    an actuator having a first anchor portion and a second anchor portion, the actuator configured to cause relative movement of the first anchor portion and the second anchor portion toward or away from one another;
    a first support member constructed to be attached to a first tissue region and adapted to be coupled to the first anchor portion of the actuator; and
    a second support member constructed to be attached to a second tissue region and adapted to be coupled to the second anchor portion of the actuator, wherein relative movement of the first anchor portion and the second anchor portion toward or away from one another results in application of a tensile force to at least one of the first tissue region and the second tissue region, the first and second tissue regions are exterior portions of a tissue conduit, the first and second support members are constructed to be attached around at least a portion of a circumference of the tissue conduit, and the actuator is configured to be positioned outside of the tissue conduit during use.

2. The apparatus of claim 1, wherein at least one of the first support member and the second support member includes an arcuate portion adapted to accommodate attachment of a plurality of sutures spaced along the circumference of the tissue conduit.

3. The apparatus of claim 1, wherein at least one of the first support member and the second support member includes a coupling portion constructed and arranged to couple the support member with the respective anchor portion of the actuator for movement of the support member along an axial direction of the tissue conduit.

4. The apparatus of claim 1, wherein at least one of the first support member and the second support member is attached to the respective anchor portion of the actuator.

5. The apparatus of claim 1, wherein at least one of the first support member and the second support member is constructed and arranged to provide a tensile force that is substantially evenly distributed along a circumference of at least one of the first tissue region and the second tissue region.

6. The apparatus of claim 1, wherein the first support member and the first anchor portion of the actuator each include an attachment structure that is complementary to one another, and the second support member and the second anchor portion of the actuator each include an attachment structure that is complementary to one another.

7. The apparatus of claim 6, wherein the first support member and the first anchor portion of the actuator are reversibly attachable to one another, and the second support member and the second anchor portion of the actuator are reversibly attachable to one another.

8. The apparatus of claim 1, wherein the first support member is constructed and arranged to be attached to a proximal esophagus portion.

9. The apparatus of claim 1, wherein the second support member is constructed and arranged to be attached to a distal esophagus portion.

10. The apparatus of claim 1, wherein the actuator includes a motor coupled to at least one of the first anchor portion and the second anchor portion.

11. The apparatus of claim 10, wherein the motor is configured to remain outside of a patient's body during relative movement of the first anchor portion and the second anchor portion toward or away from one another.

12. The apparatus of claim 10, wherein the motor is configured to remain within a patient's body during relative movement of the first anchor portion and the second anchor portion toward or away from one another.

13. The apparatus of claim 1, wherein the actuator includes a track adapted to guide directional movement of at least one of the first anchor portion and the second anchor portion.

14. The apparatus of claim 1, wherein the actuator includes a carrier adapted to cause movement of at least one of the first anchor portion and the second anchor portion toward or away from one another.

15. The apparatus of claim 1, wherein the actuator includes a rack and pinion adapted to cause movement of at least one of the first anchor portion and the second anchor portion toward or away from one another.

16. The apparatus of claim 1, wherein the actuator includes at least one flexible component coupled to at least one of the first anchor portion and the second anchor portion, for causing relative movement of the first anchor portion and the second anchor portion toward or away from one another.

17. The apparatus of claim 16, wherein the actuator includes a spool or pulley for winding of the flexible component upon relative movement of the first anchor portion and the second anchor portion toward or away from one another.

18. The apparatus of claim 1, further comprising a covering substantially surrounding the actuator.

19. The apparatus of claim 18, wherein the first and second support members are located exterior to the covering when coupled to the respective first and second anchor portions.

20. The apparatus of claim 18, wherein the covering includes a first opening to accommodate coupling of the first support member to the first anchor portion of the actuator, and a second opening to accommodate coupling of the second support member to the second anchor portion of the actuator.

21. The apparatus of claim 18, wherein the covering is adapted to be attached to surrounding tissue for providing support for the actuator.

22. The apparatus of claim 18, wherein the covering includes an elastomeric material.

23. The apparatus of claim 1, further comprising a controller configured to control the actuator to cause relative movement of the first anchor portion and the second anchor portion toward or away from one another.

24. The apparatus of claim 23, wherein the controller is in wireless communication with the actuator.

25. The apparatus of claim 1, further comprising at least one sensor configured to sense information related to the tensile force applied to at least one of the first tissue region and the second tissue region.

* * * * *